(12) United States Patent
Sierks et al.

(10) Patent No.: US 9,567,393 B2
(45) Date of Patent: *Feb. 14, 2017

(54) ANTIBODY BASED REAGENT THAT SPECIFICALLY RECOGNIZES TOXIC OLIGOMERIC FORM OF BETA-AMYLOID

(75) Inventors: Michael Sierks, Ft. McDowell, AZ (US); Srinath Kasturirangan, Germantown, MD (US)

(73) Assignee: Arizona Board of Regents, a Body Corporate of the State of Arizona Acting for and on Behalf of Arizona State University

( * ) Notice: Subject to any disclaimer, the term of this patent is extended or adjusted under 35 U.S.C. 154(b) by 347 days.

This patent is subject to a terminal disclaimer.

(21) Appl. No.: 13/821,172

(22) PCT Filed: Oct. 26, 2011

(86) PCT No.: PCT/US2011/057887
§ 371 (c)(1),
(2), (4) Date: Mar. 6, 2013

(87) PCT Pub. No.: WO2012/058308
PCT Pub. Date: May 3, 2012

(65) Prior Publication Data
US 2014/0044733 A1    Feb. 13, 2014

Related U.S. Application Data

(60) Provisional application No. 61/406,734, filed on Oct. 26, 2010, provisional application No. 61/406,728, (Continued)

(51) Int. Cl.
*C07K 16/18*    (2006.01)
*G01N 33/68*    (2006.01)
(Continued)

(52) U.S. Cl.
CPC ........... *C07K 16/18* (2013.01); *A61K 38/1716* (2013.01); *A61K 39/3955* (2013.01);
(Continued)

(58) Field of Classification Search
None
See application file for complete search history.

(56) References Cited

U.S. PATENT DOCUMENTS 8,124,076 B2   2/2012   Solomon et al.
8,409,411 B2   4/2013   Prasad et al.
(Continued)

FOREIGN PATENT DOCUMENTS

WO   WO2006014478 A1   2/2006
WO   WO2007064972 A2   6/2007
(Continued)

OTHER PUBLICATIONS

Rangan, Srinath Kasturi, et al., "Degradation of β-Amyloid by Proteolytic Antibody Light Chains," Biochem., 2003, pp. 14328-14334, vol. 42.
(Continued)

*Primary Examiner* — Jeffrey Stucker
*Assistant Examiner* — Aurora M Fontainhas
(74) *Attorney, Agent, or Firm* — Viksnins Harris & Padys PLLP

(57) ABSTRACT

The invention relates to antibodies, antibody fragments and binding agents that specifically recognizes oligomeric Aβ that is resistant to denaturation by SDS but does not bind monomeric, fibrillar or other oligomeric forms of Aβ that are generated in vitro.

8 Claims, 9 Drawing Sheets

Related U.S. Application Data filed on Oct. 26, 2010, provisional application No. 61/406,721, filed on Oct. 26, 2010.

(51) Int. Cl.
  *G01N 33/543* (2006.01)
  *A61K 38/17* (2006.01)
  *A61K 39/395* (2006.01)

(52) U.S. Cl.
  CPC ... *G01N 33/5438* (2013.01); *G01N 33/54386* (2013.01); *G01N 33/6857* (2013.01); *G01N 33/6896* (2013.01)

(56) References Cited

U.S. PATENT DOCUMENTS

| | | | |
|---|---|---|---|
| 8,507,206 | B2 | 8/2013 | Lambert et al. |
| 2005/0003396 | A1 | 1/2005 | Ozkan et al. |
| 2006/0105394 | A1 | 5/2006 | Pomara |
| 2008/0113444 | A1 | 5/2008 | Pray |
| 2008/0267952 | A1* | 10/2008 | Moir et al. ............... 424/133.1 |
| 2009/0017197 | A1 | 1/2009 | Zhang et al. |
| 2009/0081190 | A1 | 3/2009 | Stassar et al. |
| 2010/0104577 | A1 | 4/2010 | Golde et al. |

FOREIGN PATENT DOCUMENTS

| | | |
|---|---|---|
| WO | WO2009004494 A2 | 1/2009 |
| WO | WO2009089200 A2 | 7/2009 |

OTHER PUBLICATIONS

Roher, Alex E., "Morphology and toxicity of Abeta-(1-42) dimer derived from neuritic and vascular amyloid deposits of Alzheimer's disease," J. Biol. Chem., Aug. 1996, pp. 20631-20635, vol. 271, No. 34.
Santos, Alexander N., et al., "Amyloid-beta oligomers in cerebrospinal fluid are associated with cognitive decline in patients with Alzheimer's disease," J. Alzheimers Dis., 2012, pp. 171-176 vol. 29, No. 1.
Schenk, Dale, "Amaloid-Beta immunotherapy for Alzheimer's disease: The end of the beginning," Nature, Oct. 2002, pp. 824-828, vol. 3.
Selkoe, Dennis J., "Soluble oligomers of the amyloid beta-protein impair synaptic plasticity and behavior," Behav. Brain Res., Sep. 2008, pp. 106-113, vol. 192, No. 1.
Shankar, Ganesh M., et al., "Natural oligomers of the Alzheimer amyloid-beta protein induce reversible synapse loss by modulating an Nmda-type glutamate receptor-dependent signaling pathway," J. Neurosci., Mar. 2007, pp. 2866-2875, vol. 27, No. 11.
Shankar, Ganesh M., et al., "Amyloid-beta protein dimers isolated directly from Alzheimer's brains impair synaptic plasticity and memory," Nat. Med., Aug. 2008, pp. 837-842, vol. 14, No. 8.
Sheets, Michael D., et al., "Efficient construction of a large nonimmune phage antibody library: the production of high-affinity human single-chain antibodies to protein antigens," Proc. Natl. Acad. Sci., Mar. 1998, pp. 6157-6162, vol. 95, No. 11.
Shlyakhtenko, Luda S., et al., "Single-molecule selection and recovery of structure-specific antibodies using atomic force microscopy," Nanomedicine, Sep. 2007, pp. 192-197, vol. 3, No. 3.
Sierks, Michael R., et al., "CSF Levels of oligomeric alpha-synuclein and beta-amyloid as biomarkers for neurodegenerative disease," Integr. Biol., Dec. 2011, pp. 1188-1196, vol. 3, No. 12.
Solomon, Beka, "Active immunization Alzheimer's Beta-amyloid peptide using phage display technology," Vaccine, 2007, pp. 3053-3056, vol. 25.
Solomon, Beka, "Immunological Approaches for Amyloid-beta Clearance Toward Treatment for Alzheimer's Disease," Rejuvenation Res., 2008, pp. 349-357, vol. 11, No. 2.
Stains, Cliff I., et al., "Molecules that Target beta-Amyloid," Chem. Med. Chem., 2007, pp. 1674-1692, vol. 2.
Von Bernhardi, Rommy, "Immunotherapy in Alzheimer's Disease: Where Do We Stand? Where Should We Go?" J. Alz. Disease, 2010, pp. 405-421, vol. 19.
Walsh, Dominic M., "The oligomerization of amyloid beta-protein begins intracellularly in cells derived from human brain," Biochemistry, 2000, pp. 10831-10839, vol. 39, No. 35.
Walsh, Dominic M., "Naturally secreted oligomers of amyloid beta protein potently inhibit hippocampal long-term potentiation in vivo," Nature, Apr. 2002, pp. 535-539, vol. 416, No. 6880.
Walsh, Dominic M., et al., "The role of cell-derived oligomers of Abeta in Alzheimer's disease and avenues for therapeutic intervention," Biochem. Soc. Trans., Nov. 2005, pp. 1087-1090, vol. 33, Pt. 5.
Wang, Min S., et al., "Characterizing antibody specificity to different protein morphologies by AFM," Langmuir, Jan. 2009, pp. 912-918, vol. 25, No. 2.
Wang, Xiao-Ping, et al., "Conformation-dependent single-chain variable fragment antibodies specifically recognize beta-amyloid oligomers," FEBS Lett., 2009, pp. 579-584, vol. 583.
Yankner, Bruce A., "Mechanisms of Neuronal Degeneration in Alzheimer's Disease," Neuron, May 1996, pp. 921-923, vol. 15, No. 5.
Yoshihara, Tomoki, et al., "Immunoreactivity of Phage Library-derived Human Single-Chain Antibodies to Amyloid Beta Conformers In Vitro," J. Biochem., 2008, pp. 475-486, vol. 143.
Yue, Shen, et al., "The toxicity of β-amyloid is attenuated by interaction with its specific human scFv E3 in vitro," Life Sciences, 2008, pp. 1249-1255, vol. 82.
Zameer, Andleeb, et al., "Single chain Fv antibodies against the 25-35 Abeta fragment inhibit aggregation and toxicity of Abeta42," Biochemistry, Sep. 2006, pp. 11532-11539, vol. 45, No. 38.
Zameer, Andleeb, et al., "Anti-oligomeric Aβ Single-chain Variable Domain Antibody Blocks Aβ-induced Toxicity Against Human Neuroblastoma Cells," J. Mol. Biol., 2008, pp. 917-928, vol. 384.
Bothara, Manish, et al., "Nanomonitors: electrical immunoassays for protein biomarker profiling", Nanomedicine, 2008, pp. 423-436, vol. 3, No. 4.
Reddy, Ravikiran K., et al, "Nanomonitors: Protein Biosensors for Rapid Analyte Analysis," IEEE Sensors J., Jun. 2008, pp. 720-723, vol. 8, No. 6.
Venkatraman, Vinu L., et al., "Iridium oxide nanomonitors: Clinical diagnostic devices for health monitoring systems," Biosens. Bioelectron., Jun. 2009, pp. 3078-3083, vol. 24, No. 10.
Yang, Liju, et al., "AFM and impedance spectroscopy characterization of the immobilization of antibodies on indium-tin oxide electrode through self-assembled monolayer of epoxysilane and their capture of *Escherichia coli* O157:H7," Biosens. Bioelectron., Jan. 2005, pp. 1407-1416, vol. 20, No. 7.
Nanosens, Product page for Nanoproducts, available at www.nanosens.nl/product.htm. 2005.
International Search Report and Written Opinion for PCT/US2011/057877, mailed May 2, 2012 (15 pages).
International Preliminary Report on Patentability for PCT/US2011/057877, mailed May 10, 2013 (10 pages).
International Search Report and Written Opinion for PCT/US2011/057925, mailed Feb. 15, 2012 (12 pages).
International Preliminary Report on Patentability for PCT/US2011/057925, mailed Apr. 30, 2013 (8 pages).
International Search Report and Written Opinion for PCT/US2011/057904, mailed Apr. 6, 2012 (10 pages).
International Preliminary Report on Patentability for PCT/US2011/057904, mailed Apr. 30, 2013 (6 pages).
Barkhordarian, Hedieh, et al., "Isolating recombinant antibodies against specific protein morphologies using atomic force microscopy and phage display technologies," Protein Eng. Des. Sel., 2006, pp. 497-502, vol. 19, No. 11.
Callaway, Ewen, "Alzheimer's drugs take a new tack," Nature, Sep. 2012, pp. 13-14, vol. 489.

(56) References Cited

OTHER PUBLICATIONS

Caughey, Byron, et al., "Protofibrils, pores, fibrils, and neurodegeneration: separating the responsible protein aggregates from the innocent bystanders," Annu. Rev. Neurosci., 2003, pp. 267-298, vol. 26.
Cleary, James, et al., "Beta-amyloid(1-40) effects on behavior and memory," Brain Res., Jun. 1995, pp. 69-74, vol. 682, Nos. 1-2.
Cleary, James, et al., "Natural oligomers of the amyloid-beta protein specifically disrupt cognitive function," Nat. Neurosci., Jan. 2005, pp. 79-84, vol. 8, No. 1.
Cobb, Nathan J., et al, "Prion diseases and their biochemical mechanisms," Biochemistry, 2009, pp. 2574-2585, vol. 48, No. 12.
Demarest, Stephen J., et al., "Antibody therapeutics, antibody engineering, and the merits of protein stability," Curr. Opin. Drug Discov. Dev., Sep. 2008, pp. 675-687, vol. 11, No. 5.
Dodart, Jean-Cosme, et al., "Immunization reverses memory deficits without reducing brain Abeta burden in Alzheimer's disease model," Nat. Neurosci., May 2002, pp. 452-457, vol. 5, No. 5.
Elbakri, Ali, et al., "The state of antibody therapy," Hum. Immunol., Dec. 2010, pp. 1243-1250, vol. 71, No. 12.
Emadi, Sharareh, et al., "Isolation of a human single chain antibody fragment against oligomeric alpha-synuclein that inhibits aggregation and prevents alpha-synuclein-induced toxicity," J. Mol. Biol., May 2007, pp. 1132-1144, vol. 368, No. 4.
Emadi, Sharareh, et al., "Detecting morphologically distinct oligomeric forms of alpha-synuclein," Apr. 2009, J. Biol. Chem., pp. 11048-11058, vol. 284, No. 17.
Enya, Miho, et al., "Appearance of sodium dodecyl sulfate-stable amyloid beta-protein (Abeta) dimer in the cortex during aging," Am. J. Pathol., Jan. 1999, pp. 271-279, vol. 154, No. 1.
Estus, Steven, et al., Potentially Amyloidogenic, Carboxyl-Terminal Derivatives of the Amyloid Protein Precursor, Science, Feb. 1992, pp. 726-728, vol. 255, No. 5045.
Funato, Hiromasa, et al., "Presence of sodium dodecyl sulfate-stable amyloid beta-protein dimers in the hippocampus CA1 not exhibiting neurofibrillary tangle formation," Am. J. Pathol., Jul. 1999, pp. 23-28, vol. 155, No. 1.
Golde, Todd E., et al., "Processing of the Amyloid Protein Precursor to Potentially Amyloidogenic Derivatives," Science, Feb. 1992, pp. 728-730, vol. 255, No. 5045.
Gong, Yuesong, et al., "Alzheimer's disease-affected brain: presence of oligomeric A beta ligands (ADDLs) suggests a molecular basis for reversible memory loss," Proc. Natl. Acad. Sci., Sep. 2003, pp. 10417-10422, vol. 100, No. 18.
Hardy, John A., et al., "Alzheimer's disease: the amyloid cascade hypothesis," Science, Apr. 1992, pp. 184-185, vol. 256, No. 5054.
Hardy, John A., et al., "The amyloid hypothesis of Alzheimer's disease: progress and problems on the road to therapeutics," Science, Jul. 2002, pp. 353-356, vol. 297, No. 5580.
Harper, James D., et al., "Models of amyloid seeding in Alzheimer's disease and Scrapie: mechanistic truths and physiological consequences of the time-dependent solubility of amyloid proteins," Annu. Rev. Biochem., 1997, pp. 385-407, vol. 66.
Harper, James D., et al., "Observation of metastable AB amyloid protofibrils by atomic force microscopy," Chem. Biol., Feb. 1997, pp. 119-125, vol. 4, No. 2.
Hudson, Peter J., et al., "Engineered antibodies," Nat. Med., 2003, pp. 129-134, vol. 9.
Jain, Maneesh, et al., "Engineering antibodies for clinical applications," Trends Biotechnol., Jul. 2007, pp. 307-316, vol. 25, No. 7.
Kang, Jie, et al., "The precursor of Alzheimer's disease amyloid A4 protein resembles a cell-surface receptor," Nature, Feb. 1987, pp. 733-736, vol. 325, No. 6106.
Kang, Christine K., et al., "Identification of peptides that specifically bind Aβ1-40 amyloid in vitro and amyloid plaques in Alzheimer's disease brain using phage display," Neurobiol. Disease, 2003, pp. 146-156, vol. 14.
Kasturirangan, Srinath, et al., "Nanobody specific for oligomeric beta-amyloid stabilizes non-toxic form," Neurobiol. Aging, Jul. 2012, pp. 1320-1328, vol. 33, No. 7.
Kawarabayashi, Takeshi, et al., "Dimeric amyloid beta protein rapidly accumulates in lipid rafts followed by apolipoprotein E and phosphorylated tau accumulation in the Tg2576 mouse model of Alzheimer's disease," J. Neurosci., Apr. 2004, pp. 3801-3809, vol. 24, No. 15.
Kotilinek, Linda A., et al., "Reversible memory loss in a mouse transgenic model of Alzheimer's disease," J. Neurosci., Aug. 2002, pp. 6331-6335, vol. 22, No. 15.
Lafaye, Pierre, et al., "Single-domain antibodies recognize selectively small oligomeric forms of amyloid β, prevent Aβ-induced neurotoxicity and inhibit fibril formation," Mol. Immunol., 2009, pp. 695-704, vol. 46.
Lambert, M. P., et al., "Diffusible, nonfibrillar ligands derived from Abeta1-42 are potent central nervous system neurotoxins," Proc. Natl. Acad. Sci., May 1998, pp. 6448-6453, vol. 95, No. 11.
Legrand, C., "Lactate dehydrogenase (LDH) activity of the cultured eukaryotic cells as marker of the number of dead cells in the medium [corrected]," J. Biotechnol., Sep. 1992, pp. 231-243, vol. 25, No. 3.
Lemere, Cynthia A., et al., "Can Alzheimer disease be prevented by amyloid-beta immunotherapy?" Nat. Rev. Neurol., Feb. 2010, pp. 108-119, vol. 6, No. 2.
Lesne, Sylvain, et al., "A specific amyloid-beta protein assembly in the brain impairs memory," Nature, Mar. 2006, pp. 352-357, vol. 440, No. 7082.
Levites, Y., et al., Generation and characterization of single—chain variable region fragments against amyloid—beta protein, Society for Neuroscience Abstract Viewer & Itinerary Planner: Abstract 133.14, 2003.
Liu, Ruitian, et al., "P4-354 Anti Beta-amyloid SCFV Inhibits ABeta Aggregation and Neurotoxicity," Neurobiol. Aging, 2004, pp. 8575-8576, vol. 25, Supp. 2. Abstract.
Liu, Ruitian, et al., "Single Chain Variable Fragments against β-Amyloid (Aβ) Can Inhibit Aβ Aggregation and Prevent Aβ-Induced Neurotoxicity," Biochem., 2004, pp. 6959-6967, vol. 43.
Lorenzo, Alfredo, et al., "Beta-amyloid neurotoxicity requires fibril formation and is inhibited by congo red," Proc. Natl. Acad. Sci., Dec. 1994, pp. 12243-12247, vol. 91, No. 25.
Manoutcharian, K., et al., "Amyloid-beta peptide-specific single chain Fv antibodies isolated from an immune phage display library," J. Neuroimmunol., 2003, pp. 12-17, vol. 145.
Marcus, W.D., et al., "Characterization of an antibody scFv that recognizes fibrillar insulin and beta-amyloid using Atomic Force Microscopy," Nanomedicine, Mar. 2008, pp. 1-7, vol. 4, No. 1.
Marks, James D., et al., "By-passing immunization. Human antibodies from V-gene libraries displayed on phage," J. Mol. Biol., Dec. 1991, pp. 581-597, vol. 222, No. 3.
Mazzucchelli, Luca, et al., "Cell-Specific Peptide Binding by Human Neutrophils," Blood, Mar. 1999, pp. 1738-1748, vol. 93, No. 5.
Mc Donald, Jessica M., et al., "The presence of sodium dodecyl sulphate-stable Abeta dimers is strongly associated with Alzheimer-type dementia," Brain, May 2010, pp. 1328-1341, vol. 133, Pt. 5.
McLean, Catriona A., "Soluble pool of Abeta amyloid as a determinant of severity of neurodegeneration in Alzheimer's disease," Ann. Neurol., Dec. 1999, pp. 860-866, vol. 46, No. 6.
Medecigo, M., et al., "Novel amyloid-beta specific scFv and VH antibody fragments from human and mouse phage display antibody libraries," J. Neuroimmunol., 2010, pp. 104-114, vol. 223.
Meli, Giovanni, et al., "Direct in Vivo Intracellular Selection of Conformation-sensitive Antibody Domains Targeting Alzheimer's Amyloid-β Oligomers," J. Mol. Biol., 2009, pp. 584-606, vol. 387.
Oddo, Salvatore, et al., "Triple-transgenic model of Alzheimer's disease with plaques and tangles: intracellular Abeta and synaptic dysfunction," Neuron, Jul. 2003, pp. 409-421, vol. 39, No. 3.
O'Hare, E., "Delayed behavioral effects following intrahippocampal injection of aggregated A beta (1-42)," Brain Res., Jan. 1999, pp. 1-10, vol. 815, No. 1.
Ono, Kenjiro, et al., "Structure-neurotoxicity relationships of amyloid beta-protein oligomers," Proc. Natl. Acad. Sci., Sep. 2009, pp. 14745-14750, vol. 106, No. 35.

(56) References Cited

OTHER PUBLICATIONS

Panza, Francesco, et al., "Immunotherapy for Alzheimer's disease: from anti-beta-amyloid to tau-based immunization strategies," Immunotherapy, Feb. 2012, pp. 213-238, vol. 4, No. 2.

Pike, Christian J., "Neurodegeneration induced by beta-amyloid peptides in vitro: the role of peptide assembly state," J. Neurosci., Apr. 1993, pp. 1676-1687, vol. 13, No. 4.

Popkov, Mikhail, et al., "Isolation of human prostate cancer cell reactive antibodies using phage display technology," J. Immunol. Methods, 2004, pp. 137-151, vol. 291.

* cited by examiner

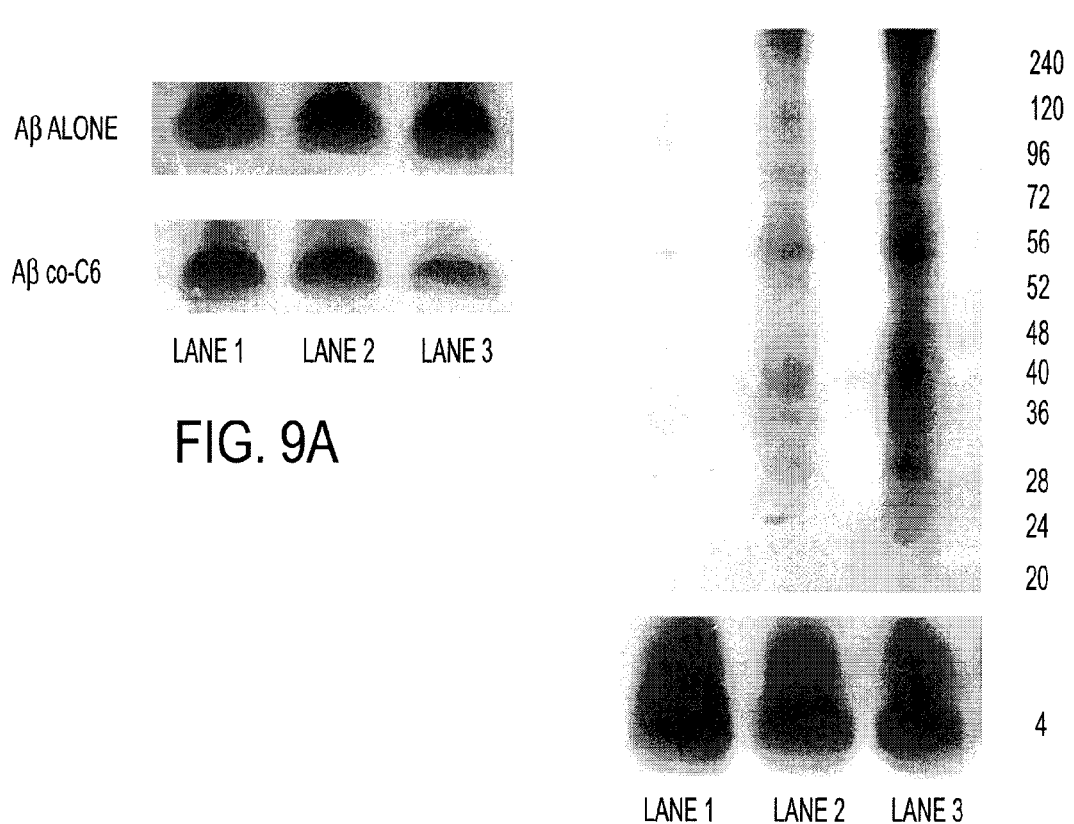

ANTIBODY BASED REAGENT THAT SPECIFICALLY RECOGNIZES TOXIC OLIGOMERIC FORM OF BETA-AMYLOID

RELATED APPLICATIONS

This patent application is a U.S. 371 application of PCT/US2011/057887, which was filed on 26 Oct. 2011, and claims the benefit of priority of U.S. application Ser. No. 61/406,734, filed 26 Oct. 2010; U.S. application Ser. No. 61/406,728, filed 26 Oct. 2010, and U.S. application Ser. No. 61/406,721, filed 26 Oct. 2010, which applications are incorporated by reference herein.

SEQUENCE LISTING

The instant application contains a Sequence Listing which has been submitted in ASCII format via EFS-Web and is hereby incorporated by reference in its entirety. Said ASCII copy, created on Nov. 7, 2011, is named 175552WO.txt and is 7,385 bytes in size.

BACKGROUND OF THE INVENTION

Aggregation and deposition of amyloid β-protein (Aβ or beta amyloid) is considered to be a primary pathological event in Alzheimer's disease (AD) (1). While the longer 42-43 amino acid Aβ forms have been implicated in the formation of amyloid plaques (2-4), the aggregation state of the peptide is critical in determining its neurotoxicity. Many different forms of Aβ have been identified and characterized including fibrils, proto-fibrils, annular structures, globular structures, amorphous aggregates and various soluble oligomers (5-9). Numerous studies indicate that small oligomeric morphologies of Aβ are the primary toxic species in AD (10). These small oligomers are also called "low-n oligomers" (i.e., dimers, trimers, or tetramers).

One type of naturally occurring oligomeric Aβ species is a low-n oligomer that is SDS-stable, and inhibits long term potentiation in mammalian hippocampus (13). The naturally occurring low-n SDS-stable Aβ oligomers cause short term memory loss in rats, one of the earliest symptom associated with AD (19), and also affect dendritic morphology in neuronal cells resulting in synaptic losses (20). Concentration levels of this SDS-stable oligomeric form correlate strongly with dementia in AD patients (14). Unlike in vitro generated Aβ, naturally occurring low-n oligomeric aggregate does not dissociate in SDS (e.g., 1-10%) or chaotropic salts such as guanidine hydrochloride (e.g., 1-10%), and cannot be pelleted from physiological fluids by ultra-centrifugation (15). The naturally occurring low-n oligomeric aggregates can be detected in brain tissue by Western blot analysis (16-17). They are also resistant to the Aβ degrading protease insulin degrading enzyme (IDE) (18).

Synthetically generated (i.e., in vitro generated) Aβ aggregates function similarly to naturally occurring Aβ species (11). Antibody fragments generated against synthetic oligomeric Aβ recognize naturally occurring oligomeric Aβ in human brain tissue (12). While intracerebral injections of synthetic Aβ oligomers exerted a deleterious effect on learned behavior in rats (21-22), these responses were delayed and the concentrations and amounts of synthetic Aβ were much higher than concentrations of naturally derived SDS-stable low-n Aβ oligomers required to interfere with the memory of a complex learned behavior (19). Together these studies clearly suggest that the naturally derived SDS-stable Aβ oligomers may be important mediators in synaptic dysfunction in early AD and that these naturally derived oligomers behave differently than in vitro derived oligomers.

Antibodies and small molecule inhibitors of Aβ aggregation have been shown to prevent spine loss induced by the SDS-stable Aβ oligomers (23-24). Since they have not been raised against a particular oligomeric form, however, anti-Aβ antibodies have a wide range of specificities, targeting different regions or multiple morphologies of Aβ. Therefore, reagents that can specifically target these naturally derived SDS-stable oligomers would be valuable tools for diagnostic and therapeutic applications for AD.

Accordingly, there exists the need for new therapies and reagents for the treatment of Alzheimer's disease, in particular, therapies and reagents capable of effecting a therapeutic and diagnostic benefit at physiologic (e.g., non-toxic) doses.

SUMMARY OF THE INVENTION

The present invention discloses an antibody or antibody fragment that specifically recognizes oligomeric Aβ that is at least partially resistant to denaturation by SDS (i.e., is SDS-stable) but does not bind monomeric or fibrillar Aβ or in vitro-generated oligomeric Aβ. As used herein, the term "antibody" includes scFv (also called a "nanobody"), humanized, fully human or chimeric antibodies, single-chain antibodies, diabodies, and antigen-binding fragments of antibodies (e.g., Fab fragments). As used herein, the term "oligomer" refers to a dimer, trimer, or tetramer. As used herein, "SDS-stable" means that the oligomeric aggregate does not dissociate into the monomer units in SDS (such as in 1-10% SDS. In exemplary embodiments, the antibody fragment does not contain the constant domain region of an antibody.

The antibody fragment described herein may be isolated according to a method comprising the steps of:
  (a) negative panning of a scFV phage library comprising serially contacting phage with:
    (i) brain derived control samples that do not contain oligomeric Aβ,
    (ii) brain-derived mononeric forms of Aβ, and
    (iii) synthetic monomeric forms of Aβ, and monitoring the binding of said phage to said synthetic synthetic monomeric forms of Aβ and repeating the negative panning until no phage was observed binding to antigen to produce an aliquot of phage that does not bind to monomeric, fibrillar or other oligomeric forms of Aβ;
  (b) positive panning of the aliquot from step (a) comprising contacting the aliquot of phage from step (a) with natural brain derived, SDS-stable oligomers of Aβ, and incubating for time sufficient to allow binding of phage to said SDS-stable oligomers of Aβ; and
  (c) eluting the bound phage particles from step (b).

In certain embodiments the observing of the binding of the phage to the synthetic monomeric forms of Aβ is by using Atomic Force Microscope (AFM) Imaging. In certain embodiments, the negative panning is repeated until less than 0-10% phage was observed by AFM imaging as binding to antigen in step (a).

In certain embodiments, the antibody fragment is less than 500 amino acids in length, such as between 200-450 amino acids in length, or less than 300 amino acids in length. In certain embodiments, the antibody fragment comprises (consists essentially of, or consists of) amino acid residues 16-292 of SEQ ID NO:1. In specific embodiments, the antibody fragment has an amino acid sequence of SEQ ID NO:1. The antibody fragment is specific for a 12-16 kDa oligomeric species of Aβ.

Also contemplated herein is a binding molecule that binds to oligomeric Aβ that is at least partially resistant to denaturation by SDS but does not bind monomeric Aβ, fibrillar Aβ or oligomeric forms of Aβ that are generated in vitro, wherein the binding molecule comprises the sequence of SEQ ID NO:1.

Another embodiment contemplates a method of inhibiting the aggregation of Aβ comprising contacting a composition that comprises Aβ monomers with an antibody, antibody fragment or binding molecule of the invention. In certain embodiments, the aggregation of Aβ is in a cell. In more specific embodiments, the aggregation of Aβ is in brain tissue. In the methods of the invention, the contacting with an antibody fragment or binding molecule decreases the rate of formation of Aβ aggregates as compared to the rate in the absence of composition or binding molecule.

Another embodiment is directed to a method of detecting the presence of Aβ in a physiological sample comprising contacting a sample with an antibody composition of the invention and determining the binding of the composition with said tissue sample wherein binding of the composition to the tissue sample is indicative of the presence of SDS-stable Aβ oligomers in the tissue sample wherein said presence of said SDS-stable Aβ oligomers is indicative of early stage AD. In certain embodiments, the physiological sample is brain tissue, serum, cerebrospinal fluid (CSF), urine or saliva.

In a further embodiment, there is a method of preventing or inhibiting the accumulation of Aβ in the brain of a mammal comprising administering to said mammal a composition comprising an antibody, antibody fragment or a binding molecule of the invention.

BRIEF DESCRIPTION OF THE DRAWINGS

FIGS. 9A-9B: C6 stabilizes SDS-stable oligomers. 50 μM Aβ was incubated alone or in the presence of 5 μM C6 nanobody. Aliquots corresponding to monomers (Lane 1), early oligomers corresponding to 3 h-1 D of aggregation (Lane 2) and late stage oligomers corresponding to 2-4 D of aggregation (Lane 3) were separated on a 10% Tris-Tricine gel followed by transfer onto a nitrocellulose membrane. The membrane was probed with 1/1000 dilution of 6E10 monoclonal antibody followed by 1/1000 dilution of goat anti-mouse IgG-HRP secondary antibody. A) Comparison of Aβ monomer levels when incubated with or without C6. B) Depletion of monomers and appearance of SDS stable oligomers when Aβ is incubated with C6.

DETAILED DESCRIPTION OF THE INVENTION

Figure 1:
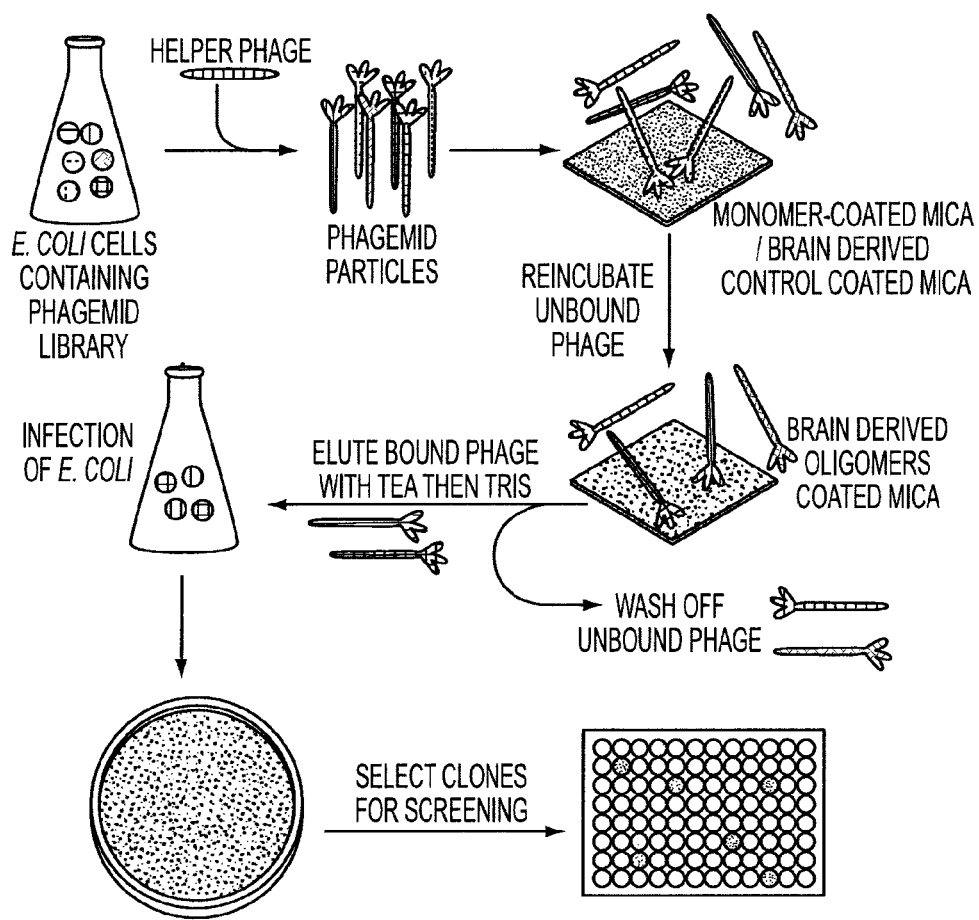
FIG. 1. Bio-panning against natural Aβ oligomers—Schematic. Panning protocol showing different steps involved in isolating scFv against low concentrations of natural brain derived Aβ oligomers.

Soluble cell-derived oligomers of Aβ have been shown to play a critical role in disrupting synaptic plasticity and behavior in Alzheimer's Disease (AD) and developing reagents against these species represents a potential therapeutic option. In the present invention, using a novel bio-panning protocol to identify single chain antibody fragments (scFv, also called nanobodies) against low (pico-molar) quantities of cell-derived Aβ dimers, the inventors identified a binding reagent with therapeutic and diagnostic properties. The method involved performing negative panning against non-desired antigens such as brain derived proteins, Aβ monomers or fibrillar Aβ. The negative panning steps were visualized by atomic force microscopy (AFM) and were continued until no more phage binding to the monomers was observed. Subsequently, positive panning was performed by adding the phage in the supernatants from the negative panning to naturally occurring low-n SDS-stable Aβ oligomers. This positive panning step resulted in isolation of phage that bound specifically to the naturally occurring low-n SDS-stable Aβ oligomers but not to monomeric Aβ, fibrillar Aβ or other cell derived proteins. Phage eluted from the oligomer mica was screened against dilutions of antigen concentrations to isolate phage having highest affinities. Clone C6 was isolated which had high expression levels, and bound specifically to brain derived low-n SDS-stable Aβ oligomers. The C6 nanobodies also recognized a 12-16 kDa Aβ fragment in cell media extracted from a human amyloid precursor over-expressing cell line, and protected the cells from intrinsic toxicity. The C6 nanobodies prevented aggregation of synthetic Aβ in vitro and stabilized the formation of toxic low-n SDS-stable Aβ oligomers. The C6 nanobodies could specifically detect Aβ aggregates in brain tissue from AD patients and also in younger transgenic mouse models of AD. Since this C6 nanobody recognized a small soluble oligomeric morphology of Aβ generated in vivo, it has potential as a diagnostic for the early detection of AD.

The inventors developed a bio-panning technique that combined phage display technology and atomic force microscopy (AFM) that enabled the inventors to isolate antibody fragments (also called nanobodies) against specific protein morphologies. Using this technology, the inventors isolated nanobodies specific for two different oligomeric morphologies of synthetic Aβ. Both of the nanobodies inhibited Aβ aggregation and toxicity towards neuronal cells, and both recognized Aβ aggregates in human AD brain tissue (25-28). Here the inventors report a modified bio-panning protocol that enables the isolation of nanobodies that specifically recognize the brain-derived SDS-stable Aβ oligomers implicated in LTP dysfunction and impairment of synaptic plasticity without also recognizing monomeric, fibrillar or synthetic oligomeric Aβ. By incorporating a series of "negative panning" steps, the inventors eliminated essentially 100% of phage binding to off-target antigens (including Aβ monomers and other brain derived proteins) and were able to isolate nanobodies to brain derived Aβ oligomers using only pico-grams of an enriched sample using a single round of bio-panning. Using this process the clone C6 was selected because it had suitable specificity and high expression levels.

The C6 nanobody specifically binds brain derived Aβ aggregates but not synthetic Aβ aggregates. Cell media from a cell line that overexpresses human amyloid precursor protein (hAAP) probed with C6 nanobodies showed a band corresponding to 16 kDa, suggesting that the C6 nanobody recognizes a tetrameric form of Aβ. C6 also recognized natural Aβ in the brain tissue from mouse models of AD, and natural Aβ in the brain tissue from human AD patients. C6 nanobodies prevented aggregation of synthetic Aβ monomers into fibrils and stabilized the formation of SDS-stable low-n oligomers that were toxic to SH-SY5Y neuroblastoma cells in vitro.

In certain embodiments, the C6 nanobody has a sequence of SEQ ID NO:1:

```
EXPIAYGSRWIVITRGPAGHGPGTAAGVGGGLVQPGGSLRL

SCAASGFTFSSYAMSWVRQAPGKGLEWVSAISGSGGSTYYADSV

KGRFTISRDNSKNTLYLQMNSLRAEDTAVYYCAKSYGSVKISCFD

YWGQSTLVTVSSGGGGSGGGGSGGGGSEIVLTQSPDSLAVSLGER

ATINCKSSQSVLYNSNNKNYLAWYQQKPGQSPELLIYWASTRESG

VPDRFSGSGSGTEFTLTISSLQAEDVAVYYCQQFYSTPPTFGQGTK

LEIKRAAAHHHHHHGAAEQKLISEED
```

In certain embodiments, the C6 nanobody lacks from 1 to 15 of the initial amino acids of SEQ ID NO:1.

In a broad sense the C6 composition of the present invention may be described as a compound that is an Aβ binding compound. This compound may therefore be used in diagnostic as well therapeutic applications and may be either administered to patients or used on patient tissue samples. In some embodiments, the C6 compositions may be used for in vivo imaging of amyloid deposits, and distinguish between neurological tissue with amyloid deposits and normal neurological tissue. As such the C6 nanobody compositions may be used to detect and quantitate amyloid deposits in diseases including, for example, Down's syndrome or familial Alzheimer's Disease. In another embodiment, the compounds may be used in the treatment or prophylaxis of neurodegenerative disorders. Also provided herein are methods of allowing the compound to distribute into the brain tissue, and imaging the brain tissue, wherein an increase in binding of the compound to the brain tissue compared to a normal control level of binding indicates that the mammal is suffering from or is at risk of developing a neurodegenerative disease such as Alzheimer's Disease.

The methods of the present invention are conducted to provide early stage diagnosis of Alzheimer's Disease. As explained herein the C6 nanobody of the invention is one that specifically recognizes recognize the brain-derived SDS-stable Aβ oligomers. Thus, compositions comprising this antibody may be used to identify the presence of this form of Aβ oligomers in a biological sample from a patient to be tested for Alzheimer's Disease wherein the presence of these forms of Aβ oligomers in the sample is indicative that the patient has or is likely to develop Alzheimer's Disease. In certain embodiments, the assay format that is used may be any assay format that typically employs antibody compositions. Thus, for example, the biological sample may be examined using immunohistology techniques, ELISA, Western Blotting, and the like.

For purposes of the diagnostic methods of the invention, the C6 composition may be conjugated to a detecting reagent that facilitates detection of the C6. For example, example, the detecting reagent may be a direct label or an indirect label. The labels can be directly attached to or incorporated into the detection reagent by chemical or recombinant methods.

In one embodiment, a label is coupled to the C6 through a chemical linker. Linker domains are typically polypeptide sequences, such as poly gly sequences of between about 5 and 200 amino acids. In some embodiments, proline residues are incorporated into the linker to prevent the formation of significant secondary structural elements by the linker. In certain embodiments, linkers are flexible amino acid subsequences that are synthesized as part of a recombinant fusion protein comprising the RNA recognition domain. In one embodiment, the flexible linker is an amino acid subsequence that includes a proline, such as Gly(x)-Pro-Gly(x) where x is a number between about 3 and about 100. In other embodiments, a chemical linker is used to connect synthetically or recombinantly produced recognition and labeling domain subsequences. Such flexible linkers are known to persons of skill in the art. For example, poly(ethylene glycol) linkers are available from Shearwater Polymers, Inc. Huntsville, Ala. These linkers optionally have amide linkages, sulfhydryl linkages, or heterofunctional linkages.

The detectable labels used in the assays of the present invention to diagnose Alzheimer's Disease, these labels are attached to the C6 nanobody, can be primary labels (where the label comprises an element that is detected directly or that produces a directly detectable element) or secondary labels (where the detected label binds to a primary label, e.g., as is common in immunological labeling). An introduction to labels, labeling procedures and detection of labels is found in Polak and Van Noorden (1997) Introduction to Immunocytochemistry, 2nd ed., Springer Verlag, N.Y. and in Haugland (1996) Handbook of Fluorescent Probes and Research Chemicals, a combined handbook and catalogue Published by Molecular Probes, Inc., Eugene, Oreg. Patents that described the use of such labels include U.S. Pat. Nos. 3,817,837; 3,850,752; 3,939,350; 3,996,345; 4,277,437; 4,275,149; and 4,366,241.

Primary and secondary labels can include undetected elements as well as detected elements. Useful primary and secondary labels in the present invention can include spectral labels such as green fluorescent protein, fluorescent dyes (e.g., fluorescein and derivatives such as fluorescein isothiocyanate (FITC) and Oregon Green™, rhodamine and derivatives (e.g., Texas red, tetrarhodimine isothiocynate (TRITC), etc.), digoxigenin, biotin, phycoerythrin, AMCA, CyDyes™, and the like), radiolabels (e.g., $^{3}$H, $^{125}$I, $^{35}$S, $^{14}$C, $^{32}$P, $^{33}$P, etc.), enzymes (e.g., horse radish peroxidase, alkaline phosphatase etc.), spectral calorimetric labels such as colloidal gold or colored glass or plastic (e.g. polystyrene, polypropylene, latex, etc.) beads. The label can be coupled directly or indirectly to a component of the detection assay (e.g., the detection reagent) according to methods well known in the art. As indicated above, a wide variety of labels may be used, with the choice of label depending on sensitivity required, ease of conjugation with the compound, stability requirements, available instrumentation, and disposal provisions.

Exemplary labels that can be used include those that use: 1) chemiluminescence (using horseradish peroxidase and/or alkaline phosphatase with substrates that produce photons as breakdown products as described above) with kits being available, e.g., from Molecular Probes, Amersham, Boehringer-Mannheim, and Life Technologies/Gibco BRL; 2) color production (using both horseradish peroxidase and/or alkaline phosphatase with substrates that produce a colored precipitate (kits available from Life Technologies/Gibco BRL, and Boehringer-Mannheim)); 3) fluorescence using, e.g., an enzyme such as alkaline phosphatase, together with the substrate AttoPhos (Amersham) or other substrates that produce fluorescent products, 4) fluorescence (e.g., using Cy-5 (Amersham), fluorescein, and other fluorescent tags); 5) radioactivity. Other methods for labeling and detection will be readily apparent to one skilled in the art.

Where the C6 nanobody-based compositions are contemplated to be used in a clinical setting, the labels are preferably non-radioactive and readily detected without the necessity of sophisticated instrumentation. In certain embodiments, detection of the labels will yield a visible signal that is immediately discernable upon visual inspection. One example of detectable secondary labeling strategies uses an antibody that recognizes Aβ amyloid fibrils in which the antibody is linked to an enzyme (typically by recombinant or covalent chemical bonding). The antibody is detected when the enzyme reacts with its substrate, producing a detectable product. In certain embodiments. enzymes that can be conjugated to detection reagents of the invention include, e.g., β-galactosidase, luciferase, horse radish peroxidase, and alkaline phosphatase. The chemiluminescent substrate for luciferase is luciferin. One embodiment of a fluorescent substrate for β-galactosidase is 4-methylumbelliferyl-β-D-galactoside. Embodiments of alkaline phosphatase substrates include p-nitrophenyl phosphate (pNPP), which is detected with a spectrophotometer; 5-bromo-4-chloro-3-indolyl phosphate/nitro blue tetrazolium (BCIP/NBT) and fast red/napthol AS-TR phosphate, which are detected visually; and 4-methoxy-4-(3-phosphonophenyl) spiro[1,2-dioxetane-3,2'-adamantane], which is detected with a luminometer. Embodiments of horse radish peroxidase substrates include 2,2'azino-bis(3-ethylbenzthiazoline-6 sulfonic acid) (ABTS), 5-aminosalicylic acid (5AS), o-dianisidine, and o-phenylenediamine (OPD), which are detected with a spectrophotometer, and 3,3,5,5'-tetramethylbenzidine (TMB), 3,3' diaminobenzidine (DAB), 3-amino-9-ethylcarbazole (AEC), and 4-chloro-1-naphthol (4C1N), which are detected visually. Other suitable substrates are known to those skilled in the art. The enzyme-substrate reaction and product detection are performed according to standard procedures known to those skilled in the art and kits for performing enzyme immunoassays are available as described above.

The presence of a label can be detected by inspection, or a detector which monitors a particular probe or probe combination is used to detect the detection reagent label. Typical detectors include spectrophotometers, phototubes and photodiodes, microscopes, scintillation counters, cameras, film and the like, as well as combinations thereof. Examples of suitable detectors are widely available from a variety of commercial sources known to persons of skill. Commonly, an optical image of a substrate comprising bound labeling moieties is digitized for subsequent computer analysis.

As noted herein throughout the C6 nanobody is targeted specifically to Aβ amyloid fibrils that are characteristic of Alzheimer's Disease. As such, the C6 nanobody also may be used to specifically target therapeutic compositions to the sites of plaque formation. In this embodiment, any therapeutic agent typically used for the treatment of Alzheimer's disease may be conjugated to C6 nanobody in order to achieve a targeted delivery of that therapeutic agent. Various drugs for the treatment of AD are currently available as well as under study and regulatory consideration. The drugs generally fit into the broad categories of cholinesterase inhibitors, muscarinic agonists, anti-oxidants or anti-inflammatories. Galantamine (Reminyl), tacrine (Cognex), selegiline, physostigmine, revistigmin, donepezil, (Aricept), rivastigmine (Exelon), metrifonate, milameline, xanomeline, saeluzole, acetyl-L-carnitine, idebenone, ENA-713, memric, quetiapine, neurestrol and neuromidal are just some of the drugs proposed as therapeutic agents for AD that can be conjugated to the C6 composition and targeted for therapeutic intervention of AD.

The C6 nanobody composition can be used in any diagnostic assay format to determine the presence of brain-derived SDS-stable Aβ oligomers. A variety of immunodetection methods are contemplated for this embodiment. Such immunodetection methods include enzyme linked immunosorbent assay (ELISA), radioimmunoassay (RIA), immunoradiometric assay, fluoroimmunoassay, chemiluminescent assay, bioluminescent assay, and Western blot, though several others are well known to those of ordinary skill. The steps of various useful immunodetection methods have been described in the scientific literature.

In general, the immunobinding methods include obtaining a sample suspected of containing a protein, polypeptide and/or peptide (in this case the SDS-stable Aβ oligomers), and contacting the sample with a first antibody, monoclonal or polyclonal (in this case C6 nanobody), in accordance with the present invention, as the case may be, under conditions effective to allow the formation of immunocomplexes.

The immunobinding methods include methods for detecting and quantifying the amount of stable Aβ oligomers component in a sample and the detection and quantification of any immune complexes formed during the binding process. Here, one would obtain a sample suspected of containing stable Aβ oligomers, and contact the sample with an C6 antibody fragment, and then detect and quantify the amount of immune complexes formed under the specific conditions.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to, any antigens present. After this time, the sample-antibody composition, such as a tissue section, ELISA plate, dot blot or western blot, will generally be washed to remove any non-specifically bound antibody species, allowing only those C6 nanobody molecules specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. U.S. patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody and/or a biotin/avidin ligand binding arrangement, as is known in the art.

As noted above, the C6 nanobody may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the C6 nanobody is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection designed by Charles Cantor uses two different antibodies. A first step biotinylated, monoclonal or polyclonal antibody (in the present example the C6 nanobody) is used to detect the target antigen(s), and a second step antibody is then used to detect the biotin attached to the complexed nanobody. In this method the sample to be tested is first incubated in a solution containing the first step nanobody. If the target antigen is present, some of the nanobody binds to the antigen to form a biotinylated nanobody/antigen complex. The nanobody/antigen complex is then amplified by incubation in successive solutions of streptavidin (or avidin), biotinylated DNA, and/or complementary biotinylated DNA, with each step adding additional biotin sites to the nanobody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

As detailed above, immunoassays, in their most simple and/or direct sense, are binding assays. Certain preferred immunoassays are the various types of enzyme linked immunosorbent assays (ELISAs) and/or radioimmunoassays (RIA) known in the art. Immunohistochemical detection using tissue sections is also particularly useful. However, it will be readily appreciated that detection is not limited to such techniques, and/or western blotting, dot blotting, FACS analyses, and/or the like may also be used.

The diagnostic assay format that may be used in the present invention could take any conventional format such as ELISA or other platforms such as luminex or biosensors. The present invention shows the sequence of the C6 nanobody. This sequence can readily be modified to facilitate diagnostic assays, example a tag (such as GFP) can be added to C6 nanobody to increase sensitivity. In one exemplary ELISA, antibodies (in the present case the C6 nanobodies) are immobilized onto a selected surface exhibiting protein affinity, such as a well in a polystyrene microtiter plate. Then, a test composition suspected of containing the SDS stable low-n Aβ oligomers, such as a clinical sample (e.g., a biological sample obtained from the subject), is added to the wells. After binding and/or washing to remove non-specifically bound immune complexes, the bound antigen may be detected. Detection is generally achieved by the addition of another antibody that is linked to a detectable label. This type of ELISA is a simple "sandwich ELISA." Detection may also be achieved by the addition of a second antibody, followed by the addition of a third antibody that has binding affinity for the second antibody, with the third antibody being linked to a detectable label.

In another exemplary ELISA, the samples suspected of containing the antigen are immobilized onto the well surface and/or then contacted with binding agents (e.g., C6 nanobodies). After binding and/or washing to remove non-specifically bound immune complexes, the bound anti-binding agents are detected. Where the initial binding agents are linked to a detectable label, the immune complexes may be detected directly. Again, the immune complexes may be detected using a second antibody that has binding affinity for the first binding agents, with the second antibody being linked to a detectable label.

Another ELISA in which the antigens are immobilized, involves the use of antibody competition in the detection. In this ELISA, labeled antibodies (or nanobodies) against an antigen are added to the wells, allowed to bind, and/or detected by means of their label. The amount of an antigen in an unknown sample is then determined by mixing the sample with the labeled antibodies against the antigen during incubation with coated wells. The presence of an antigen in the sample acts to reduce the amount of antibody against the antigen available for binding to the well and thus reduces the ultimate signal. This is also appropriate for detecting antibodies against an antigen in an unknown sample, where the unlabeled antibodies bind to the antigen-coated wells and also reduces the amount of antigen available to bind the labeled antibodies.

Irrespective of the format employed, ELISAs have certain features in common, such as coating, incubating and binding, washing to remove non-specifically bound species, and detecting the bound immune complexes.

In coating a plate with either SDS-stable low-n Aβ oligomers or C6 nanobodies, one will generally incubate the wells of the plate with a solution of the antigen or nanobodies, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the SDS stable low-n Aβ oligomers and/or C6 nanobody composition with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. An example of a washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. This may be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

In various aspects of the invention, it will be desirable to further subject patients to more traditional AD diagnostic approaches. Such general approaches for diagnosis are set out below.

The diagnosis of both early (mild) cognitive impairment and AD are based primarily on clinical judgment. However, a variety of neuropsychological tests aid the clinician in reaching a diagnosis. Early detection of only memory deficits may be helpful in suggesting early signs of AD, since other dementias may present with memory deficits and other signs. Cognitive performance tests that assess early global cognitive dysfunction are useful, as well as measures of working memory, episodic memory, semantic memory, perceptual speed and visuospatial ability. These tests can be administered clinically, alone or in combination. Examples of cognitive tests according to cognitive domain are shown as examples, and include "Digits Backward" and "Symbol Digit" (Attention), "Word List Recall" and "Word List Recognition" (Memory), "Boston Naming" and "Category Fluency" (Language), "MMSE 1-10" (Orientation), and "Line Orientation" (Visuospatial). Thus, neuropsychological tests and education-adjusted ratings are assessed in combination with data on effort, education, occupation, and motor and sensory deficits. Since there are no consensus criteria to clinically diagnose mild cognitive impairment, various combinations of the above plus the clinical examination by an experienced neuropsychologist or neurologist are key to proper diagnosis. As the disease becomes more manifest (i.e., becomes a dementia rather than mild cognitive impairment), the clinician may use the criteria for dementia and AD set out by the joint working group of the National Institute of Neurologic and Communicative Disorders and Stroke/AD and Related Disorders Association (NINCDS/ADRDA). On occasion, a clinician may request a head computed tomography (CT) or a head magnetic resonance imaging (MRI) to assess degree of lobar atrophy, although this is not a requirement for the clinical diagnosis.

As noted above, there are various drugs that are presently in use or under development for the treatment of Alzheimer's Disease. The present invention contemplates the use of C6-nanobody based "diagnostic" methods to further assess the efficacy of treatments. Given the role of Aβ in AD, the ability of a particular therapy to reduce the amount of Aβ will be indicative of an effective treatment, since low amounts of Aβ will presumably reduce the rate or development of plaques, thereby impeding the progression of the disease.

The present invention may involve the use of pharmaceutical compositions which comprise an agent conjugated to a C6 nanobody for delivery into a subject having Alzheimer's disease. Such an agent will ideally be formulated into a pharmaceutically acceptable carrier. As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art. Except insofar as any conventional carrier is incompatible with the active ingredient, its use in the therapeutic or pharmaceutical compositions is contemplated.

EXAMPLES

Materials and Methods

Phage Display scFv Library.

The Sheets phage display scFv library comprising over $10^{12}$ different scFv fragments was provided by Dr Yu (Eunice) Zhou, Department of Anesthesia, University of San Francisco (29).

Phage Production.

Production of phage from the Sheets library was performed essentially as described (30). Briefly, *E. coli* TG1 cultures in the exponential phase were infected with helper phage VCSM13 (Strategene) at a ratio of 1:50 (number of bacterial cells/phage particles) for 30 minutes at 37° C. without shaking. Cultures were grown for 1-2 hr at 37° C. in the presence of 100 µg/mL ampicillin and 25 µg/mL kanamycin for phage production followed by centrifugation at 3000×g for 20 minutes. The pellet was removed and resuspended in 1 L 2×YT with 100 µg/mL ampicillin and 25 µg/mL kanamycin, and grown overnight at 30° C. Phage were purified from the supernatant by polyethylene glycol (PEG) and NaCl precipitation and resuspended in PBS (phosphate-buffered saline) and used for panning.

Brain Derived Antigens.

The brain derived antigens were a generous gift from Dr Dennis Selkoe (Harvard Medical School, Boston). A 40 ng aliquot of enriched brain derived samples containing SDS-stable Aβ oligomers or Aβ monomers were obtained as lyophilized powder. Prior to the bio-panning experiments, the samples were re-suspended in TBS buffer to a final Aβ concentration of 5 nM, aliquoted, and stored at −20° C. Brain samples from which Aβ has been completely depleted by immunoprecipitation were used as a control.

Preparation of Synthetic Aβ.

Aβ40 was synthesized in the Proteomics and Protein Chemistry Laboratory at Arizona State University, purified by HPLC, lyophilized and stored as its Trifluoroacetate salt Aβ40 at −20° C. Samples were prepared as previously described (28). Briefly, Aβ40 was solubilized in 1,1,1,3,3,3-hexafluoro-2-propanol (HFIP) at a concentration of 1 mg/mL to avoid aggregates. Aliquots of 250 µL were air dried and stored at −20° C. Prior to use, the aliquots of monomeric Aβ were re-suspended in dimethyl-sulfoxide (DMSO) and diluted to final concentration in Tris-HCl buffer (20 mM Tris, 150 mM NaCl, pH 7.5).

Atomic Force Microscope (AFM) Imaging.

AFM analysis was performed as described previously (31). Samples were deposited on mica, dried and imaged in air using a MultiMode AFM NanoScope IIIA system (Veeco/Digital Instruments, Santa Barbara, Calif.) operating in tapping mode using silicon probes (Model: OTESPA, Veeco, Santa Barbara, Calif.) (31).

Bio-panning Against Natural Brain Derived Antigen. The bio-panning process was performed in 2 steps. The first step, referred to as "Negative panning" was used to eliminate phage that bind to non-desired antigen. The second step, "Positive panning" was used to isolate phage that bind the target antigen (FIG. 1).

1. Negative Panning.

Negative panning was performed to eliminate phage binding to non-desired antigens. A 1 ng aliquot of brain derived control proteins, 1 ng of brain derived monomers and 1 µg of synthetic monomers were deposited on multiple pieces of mica and air dried. A 100 µL aliquot of amplified phage containing $10^{12}$ phage units was serially added first to the brain derived control, next to brain derived monomers, and finally to multiple pieces of synthetic monomers in 25 µl aliquots. The phage was allowed to incubate with each piece of antigen coated mica for 10 min before removal and addition to the next sample. The negative panning steps were performed in duplicate with one set used for panning and the second set used for AFM imaging to monitor the panning process. Serial addition of phage to mica substrates containing the synthetic Aβ monomer samples was continued until no phage was observed binding to antigen by AFM analysis. Aliquots of 1×PBS were periodically added to restore phage solution volume lost due to evaporation from mica surface.

2. Positive Panning.

A 1 ng aliquot of natural brain derived SDS-stable Aβ oligomers was deposited onto mica and air dried. After all the non-binding and non-specific binding phage were eliminated in the negative panning steps, a 20 µL aliquot of remaining phage was added to mica surface, incubated for 10 min and then sequentially washed with 2 mL PBS-0.1% Tween-20, 2 mL PBS and 2 mL water and then air dried. This positive panning step was performed in duplicate, with one set used for the panning steps and the second set used for AFM imaging to monitor the panning process. Bound phage particles were eluted and recovered as previously described (25, 27).

Selection of High Affinity Clones.

Approximately 400 clones were recovered from the positive panning step and each was individually grown in 96 well plates. Phage production from the individual clones was induced by addition of helper phage as previously described. Serial dilutions of the natural brain derived Aβ oligomers (1/10-1/10,000) were deposited on mica. Phage from all 400 clones were pooled and added to each of the mica samples. Unbound phage were washed off with 2 mL PBS-0.1% Tween-20 and water and remaining phage was visualized by AFM. Phage was eluted from each of the dilutions as described above and used to infect *E. coli* TG1 and plated onto LB agar plates. Single clones were picked from the lowest dilution plate, plasmid DNA was isolated and checked by sequence analysis to verify sequence of the isolated nanobodies.

Dot Blot Assay to Screen for Expression Levels.

To check expression levels, plasmid DNA from the positive clones identified above were transformed into the non-suppressor *E. coli* HB2151 for production of soluble nanobody. Individually selected clones were grown and nanobody production was induced by addition of 1 mM isopropyl-β-D-thiogalactopyranoside (IPTG) as described earlier (30). A 5 µl aliquot of the supernatant and lysate fractions from the different clones were deposited onto a gridded nitrocellulose membrane. The membrane was blocked with 5% Milk-PBS (5 g Carnation nonfat dry milk in 100 ml PBS buffer) for at least one hour at room temperature followed by incubation overnight with a 1:1000 dilution of the primary anti-myc tag antibody 9E10 (Sigma). Immunoreactivity was detected after a 1-h incubation using a 1:1000 dilution of the secondary anti-mouse IgG HRP antibody (Sigma). The membrane was stained with 3.3'-Diaminobenzidine Tetrahydrochloride (DAB) solution (Sigma). One phage clone, which encoded scFV C6 (also called "nanobody C6") was selected for further experiments based on its higher expression levels.

Binding Specificity by Phage Assay.

To confirm binding specificity of C6 nanobody to brain derived oligomers, phage encoding the C6 nanobody, as well as phage encoding a nanobody specific for a synthetic oligomeric morphology of Aβ, A4, were produced from E. coli TG-1 essentially as described (25, 27). Purified phage were added to naturally-derived or synthetically-derived Aβ oligomers on the mica surface, and phage binding to the antigen was visualized by AFM.

Production and Purification of Soluble Nanobody.

To express and purify soluble nanobody, nucleic acid encoding C6 nanobody was first cloned into a pIT2 E. coli expression vector, and transformed into E. coli Hb2151. The supernatant and cell lysate from a 1 L culture were combined and concentrated in a tangential flow filter (Millipore) using a 10 kDa filter membrane (Millipore). The concentrated supernatant/lysate was used for dot blot and western blot assays.

For nanobody purification, a 6×His tagged nanobody was purified by mixing with 1 ml Nickel NTA sepharose beads (Qiagen, CA) for 2 hours, followed by elution with an imidazole gradient. Fractions containing nanobodies were pooled and dialyzed into 1×PBS. Protein expression and purity was checked with SDS-PAGE and western blotting. A bicinchonic acid (BCA) protein assay (Sigma) was used to determine nanobody concentration as previously described (28).

Culture of Human APP Over-Expressing Cells.

The C6 nanobody was tested for its ability to recognize naturally derived Aβ oligomers secreted by a Chinese hamster ovary (CHO) cell line stably transfected with cDNA encoding mutant human APP751 (7PA2). The 7PA2 cells were a kind gift from Dr. Dennis Selkoe (Harvard Medical School, Boston). Cells were grown in Dulbecco Modified Eagle medium (DMEM) containing 10% fetal bovine serum, 1% L-glutamine and 1% penicillin/streptomycin (Gibco). Selection for mutant APP expressing cells was performed using 1 mg/ml G-418 (Calbiochem), an amyloglycoside antibiotic. Once the cells reach 95% confluence, 7PA2 cells were plated onto 6 well plates and used for further studies.

Detection of Aβ Expressed by Human APP Over-Expressing Cells.

The 7PA2 cells were grown for 2 days after which the cell culture media was removed and concentrated. Total protein concentration was determined by BCA and 25 μg of cell culture media was separated on a 10% Tris/Tricine gel and transferred onto a 0.2 nitro-cellulose membrane (Bio-Rad). The membrane was probed for 24 hours with the concentrated supernatant/lysate containing C6 nanobody. The membrane was then incubated overnight with a 1/1000 dilution of primary anti-myc tag antibody. Immunoreactivity was detected following a 1-hour incubation with a 1/1000 dilution of a HRP conjugated goat anti-mouse IgG as secondary antibody. The membrane was stained with DAB solution as described above (Sigma).

Aβ Aggregation Assay.

Aggregation of monomeric Aβ, prepared as described above, was initiated by dilution in Tris-HCl buffer to a concentration of 50 μM and incubation in a 37° C. incubator. For co-incubation studies of Aβ with C6 nanobody, a 50 μM solution of monomeric Aβ was incubated with 5 μM C6 at 37° C. Aliquots were removed at selected time intervals for further analysis.

Thioflavin T (ThT) Fluorescence Assay.

ThT fluorescence assay was performed essentially as described (42). Fluorescence intensity was monitored at an excitation wavelength of 450 nm and an emission wavelength of 482 nm with a Shimadzu PF-3501PC spectrofluorophotometer (Shimadzu, Japan) using 1 cm light-path quartz cuvettes with both excitation and emission bandwidths of 5 nm (27-28, 32). All ThT fluorescence experiments were performed in triplicate. The standard errors were analyzed with Excel.

Tris-Tricine SDS-PAGE and Western-Blot.

Western blot analysis was used to characterize the Aβ species generated upon co-incubation with C6 nanobody. Aliquots of the Aβ sample incubated with or without C6 nanobody corresponding to different time points of aggregation were removed and separated on a 10% Tris/Tricine gel and transferred onto a 0.2 μm nitro-cellulose membrane (Bio-Rad). The membrane was probed for 24 hours with a 1/1000 dilution mouse monoclonal antibody 6E10 (Calbiochem, USA) which recognizes the N-terminus of the Aβ peptide and immunoreactivity was detected following a 1-hour incubation with a 1/1000 dilution of a HRP conjugated goat anti-mouse IgG as secondary antibody to determine monomeric and oligomeric Aβ levels in the aggregated samples.

SH-SY5Y Neuroblastoma Cell Toxicity Assay.

The human neuroblastoma cell line SH-SY5Y was obtained from the American Tissue Culture Collection (USA). Cells were cultured as previously described (27-28). To test for toxicity, a 5 μL aliquot of the Aβ samples corresponding to different time points of aggregation with or without C6 nanobody was added to the cells and incubated for 48 hours. Cytotoxicity was measured by Lactose dehydrogenase (LDH) release assay (Sigma) as described (26-28, 32). Three wells were used for each sample, and each experiment was performed in triplicate. The data are reported as the percentage of LDH released compared to the LDH released from wells with Tris-HCl buffer alone (26, 32-33). The standard errors were analyzed with Excel.

Brain Dot Blot Assays.

Mouse brain tissue from wild type and triple transgenic (3× Tg) mice were generously provided by Dr John Valla (Barrow Neurological Institute, St. Josephs Hospital, Phoenix, Ariz.). The brain tissue was weighed on ice and 4 volumes of homogenization buffer (50 mM Tris-HCL, 10 mM EDTA pH 7.5) with 1% SDS was added followed by sonication of the samples. A 1/100 dilution of the protease inhibitor cocktail (Halt Protease inhibitor, Pierce) was added and the samples were centrifuged at 13,000 rpm long enough to remove any insoluble material (typically 15-45 min at 4° C.). The resulting extracts were separated on a 10% Tris/Tricine gel followed by transfer onto a 0.2 μm nitrocellulose membrane and probed with C6 nanobody as described.

Human brain sections were generously provided by Dr. Thomas Beach (Civin Laboratory for Neuropathology, Sun Health Research Institute, Sun City, Ariz.). Brain tissue from non-diseased (ND) or Alzheimer's disease (AD) brains were homogenized and 12 μg aliquots were applied to a gridded nitrocellulose membrane as previously reported (28). Staining intensities of the blot were quantified using ImageJ software.

Results

Bio-Panning Against Naturally Derived Aβ Oligomers.

Figure 2A:
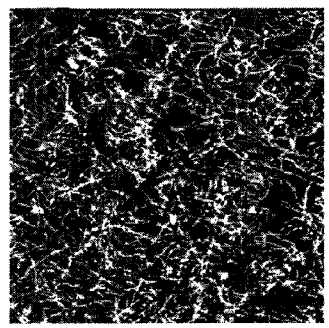
FIGS. 2A-2F. Bio-panning process visualized by AFM. Serial negative panning against A) 1 ng brain derived proteins from which Aβ has been depleted; B) 1 ng brain derived Aβ monomer; and multiple pieces containing 1 μg synthetic Aβ monomers. Panning process was visualized by AFM until no phage binding to synthetic monomers was observed. C) 1st synthetic monomer mica; D) 3rd synthetic monomer mica; E) 5th synthetic monomer mica. F) Recovered phage from last monomer mica was added to mica containing 1 ng dimer sample. Scale bar represents 1 μm.
Figure 2B:
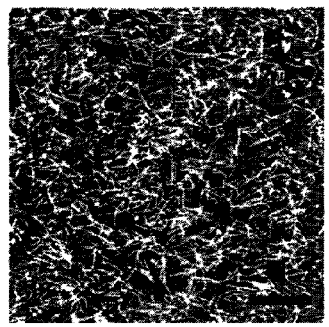
Figure 2C:
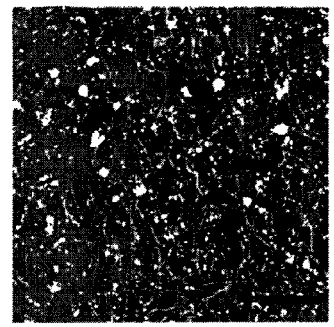
Figure 2D:
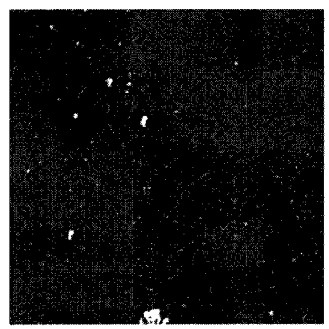
Figure 2E:
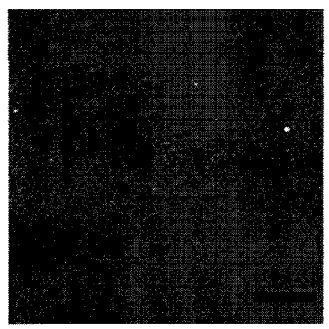
Figure 2F:
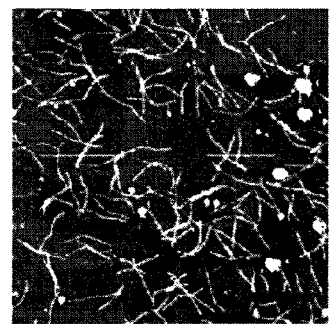
Figure 3A:
FIGS. 3A-3D. Phage from 400 clones binds specifically to natural Aβ oligomers. Phage was produced from the 400 clones obtained after the bio-panning process, and added to A) 1 ng Aβ depleted brain sample; B) 1 ng brain derived Aβ monomer; C) 1 μg synthetic Aβ monomer; D) 1 ng brain derived Aβ oligomers. Scale bar represents 1 μm.
Figure 3B:
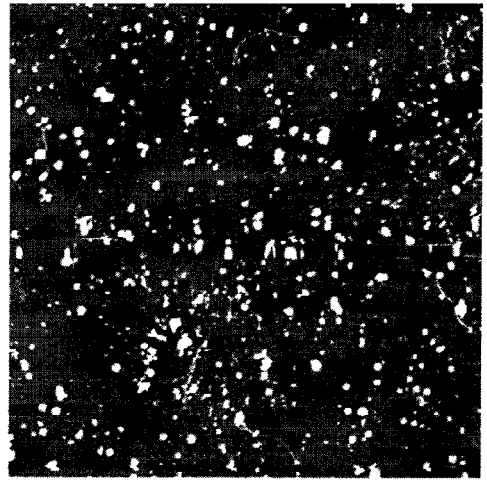
Figure 3C:
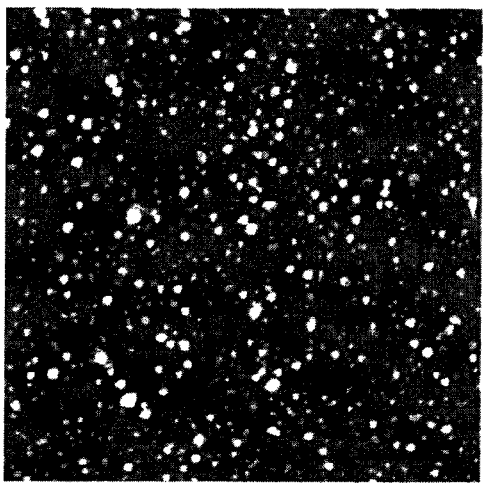
Figure 3D:
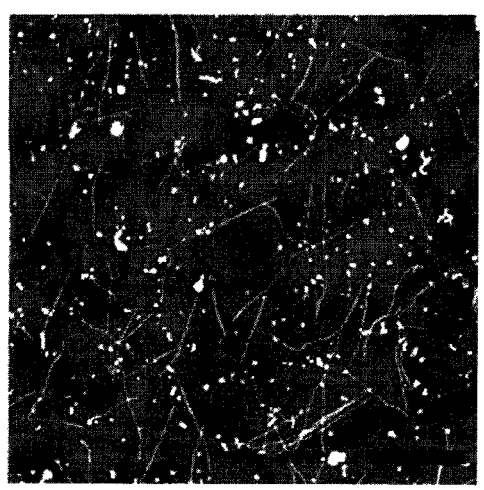

Serial negative panning performed against brain derived proteins from which Aβ has been depleted (FIG. 2A), brain-derived monomer coated mica (FIG. 2B) and 5 pieces of mica coated with synthetic Aβ monomers (FIG. 2C-E) resulted in elimination of virtually 100% of phage binding to these off-target antigens. The remaining phage aliquot from the last synthetic monomer coated mica was then added to mica coated with the brain derived SDS-stable Aβ oligomers (FIG. 2F). Approximately 400 single clones were recovered from the positive panning step.

Phage Recovered from Panning Binds Specifically to Brain Derived Oligomers.

We verified that phage recovered from the positive panning steps specifically bound SDS-stable oligomeric Aβ, but not to other, off-target antigens. Pooled phage from the approximately 400 recovered clones showed abundant binding to the brain derived Aβ oligomers, but not to monomeric Aβ or other brain derived proteins (FIG. 3).

Selection for High Affinity Phage.

To select phage with the highest affinity for oligomeric Aβ, we added an aliquot of the pooled phage from the 400 recovered clones to serial dilutions of brain derived Aβ oligomers. At low antigen concentrations, high affinity clones should preferentially bind over low affinity variants. Phage recovered from the mica samples containing 10 pg of brain derived Aβ oligomers were used for further analyses.

Production of Soluble Nanobody.

Figure 4:
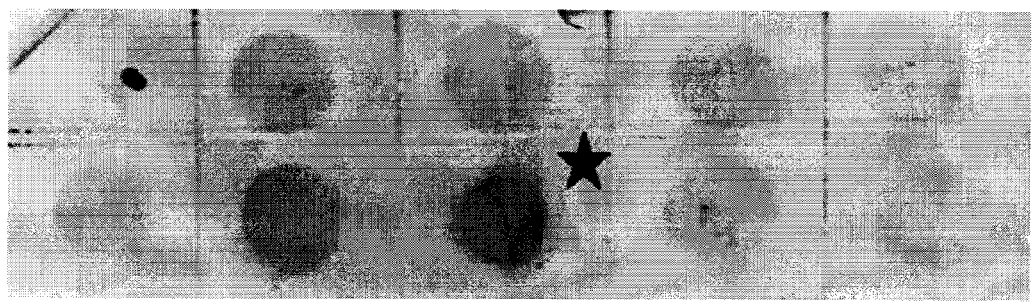
FIG. 4. Dot-blot to determine expression levels of isolated clones. Phage binding to the 10 pg brain derived dimers were eluted and transformed into Hb2151 competent cells. Single clones were picked and tested for levels of soluble scFv expression by dot blot analysis. The clone with the strongest expression (★) C6, was picked for further study.

DNA sequence analysis indicated that there were 18 distinct clones from the 30 clones recovered from the mica sample containing 10 pg of brain derived Aβ. Expression levels of the 18 clones were analyzed and clone C6 was selected for further studies based on its high expression (FIG. 4).

C6 Phage Specifically Recognizes Brain Derived Oligomers.

Figure 5A:
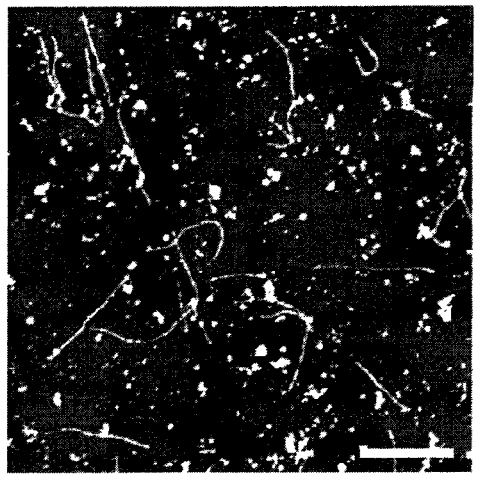
FIGS. 5A-5D. C6 specifically recognizes brain derived oligomers. Binding of C6 phage to A) natural brain derived oligomers and B) 3D synthetic Aβ aggregates was compared to binding of A4 to the same samples (C, D). Scale bar represents 1 μm.
Figure 5B:
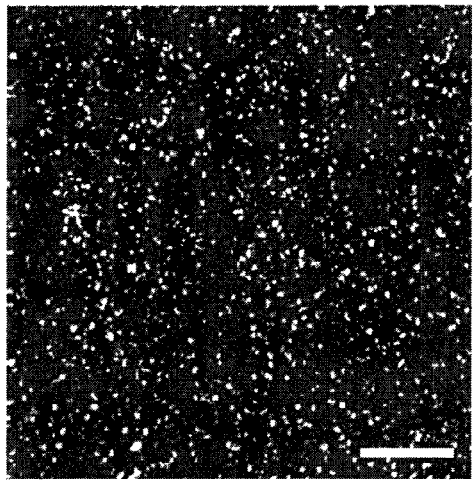
Figure 5C:
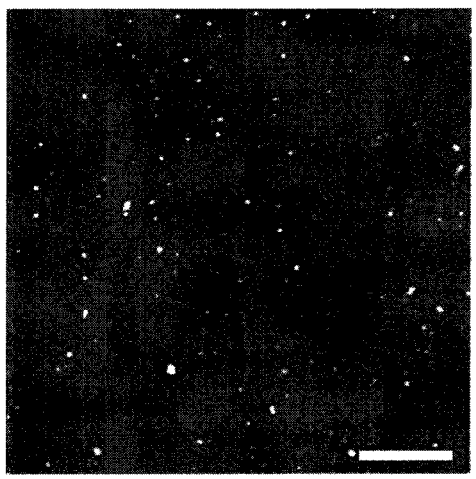
Figure 5D:
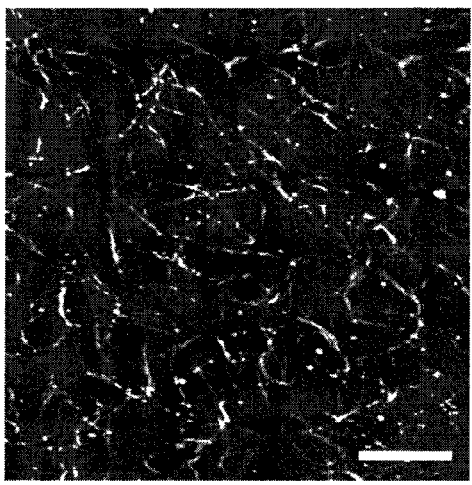

We verified that C6 phage specifically bound brain derived Aβ oligomers and did not bind other brain derived proteins or synthetic Aβ oligomers. C6 phage specifically bound natural brain derived oligomers but not synthetic Aβ aggregates corresponding to 3 days of aggregation (FIG. 5A-B). In contrast, a previously described nanobody that specifically recognized a synthetic oligomeric form of Aβ, A4, bound the 3D Aβ aggregates but did not bind the brain derived Aβ oligomers recognized by C6 (FIG. 5C-D).

Purification of C6 Nanobody.

Soluble protein from the C6 phage was expressed and purified by metal ion chromatography. Purified protein showed the expected 29 kDa band corresponding to a full length scFv (data not shown).

C6 Recognizes an Oligomeric Aβ Species Produced by 7PA2 Cells.

Figure 6:
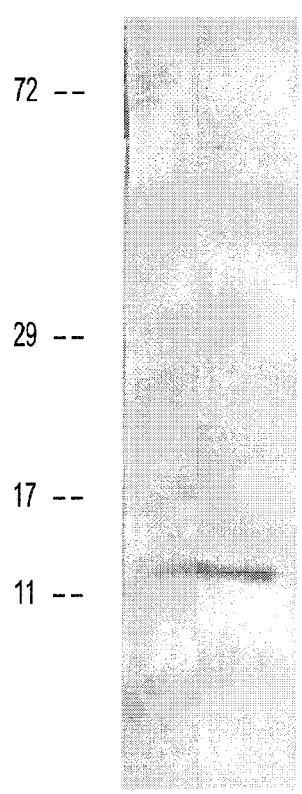
FIG. 6. C6 nanobody detects Aβ oligomers in 7PA2 cell medium. When 25 μg of the cell media was probed with C6 nanobody, a band of around 12-16 kDa could be detected, corresponding to trimeric or tetrameric morphology of Aβ.

When cell supernatant from hAPP over-expressing 7PA2 cells was analyzed by western blot probed with C6 nanobody, a 12-16 kDa band could be detected, corresponding to either an SDS-stable trimeric or tetrameric aggregate of Aβ (FIG. 6).

C6 Inhibits Aggregation of Aβ.

Figure 7:
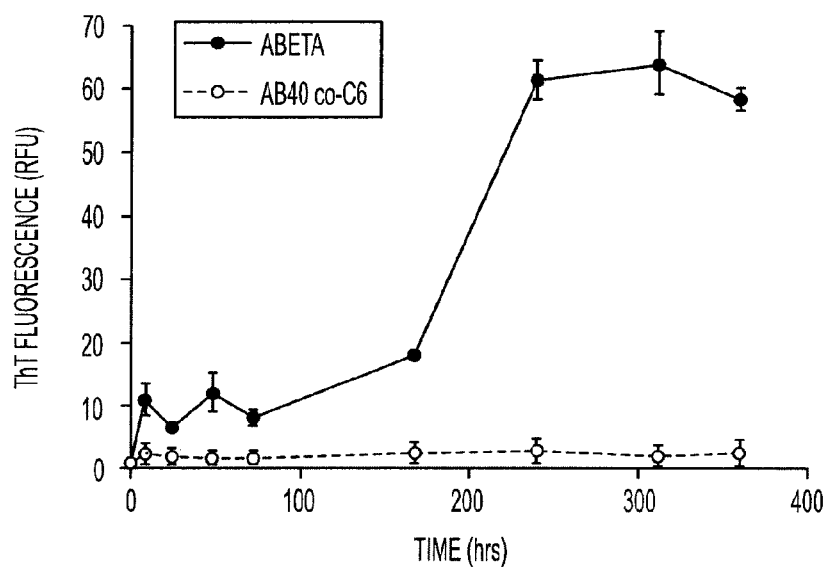
FIG. 7. ThT fluorescence assay. Aggregation of 50 μM Aβ incubated with and without 5 μM C6 was monitored by ThT fluorescence. Each experiment was performed in triplicate.
Figures 8A, 8B, 8C, 8D:
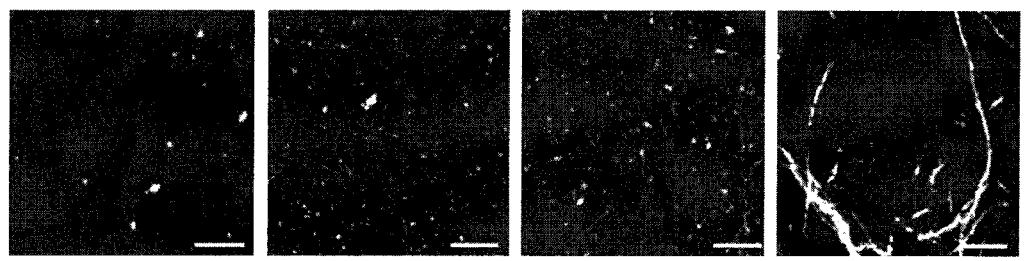
FIGS. 8A-8H. Morphology of Aβ incubated with or without C6. AFM images of 50 μM Aβ incubated without C6 for A) 0 hour, B) 3 day, C) 7 days, D) 10 days; or with C6 for E) 0 hour, F) 3 day, G) 7 days, H) 10 days. Scale bar represents 1 μm.
Figures 8E, 8F, 8G, 8H:
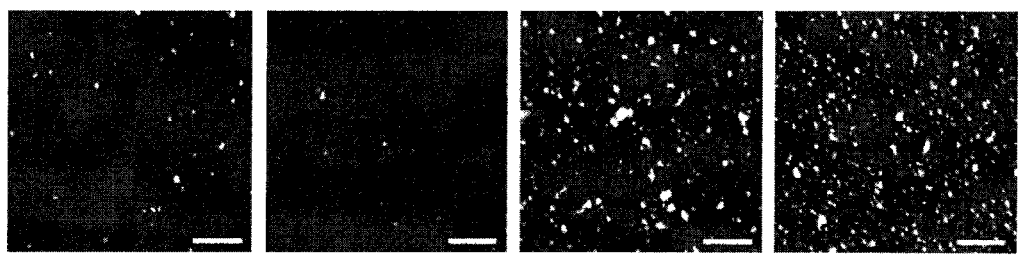

The inventors next determined whether the C6 nanobody could alter in vitro aggregation of Aβ. Incubation of Aβ alone showed a typical time-dependent increase in ThT fluorescence reaching a plateau after 10 days when fibrils are formed, while co-incubation of Aβ with C6 nanobody dramatically inhibited aggregation, as evidenced by both ThT staining (FIG. 7) and AFM analysis (FIG. 8).

Height Distribution Analyses.

To determine the size of the Aβ aggregates stabilized upon incubation with the C6 nanobody, we performed a height distribution analysis of the AFM images obtained from the samples taken at different time points with Aβ incubated alone and Aβ co-incubated with C6 nanobody. When incubated alone, Aβ aggregates show a continual increase in height with time, starting with heights <1 nm at t=0 h, presumably corresponding to monomeric Aβ, and increasing steadily with time, whereas heights >4 nm corresponding to fibrillar Aβ predominate after 7 days (Table 1A). In contrast, when Aβ is co-incubated with C6 nanobody, the aggregation rate of Aβ is dramatically altered, with particle heights remaining essentially constant with the vast majority of particles having heights between 2-3 nm, even after 7 days of aggregation (Table 1B).

Table 1Aβ40 incubated alone (A) or co-incubated with 5 µM C6 nanobody (B) for 8 days. Height distribution analysis of AFM samples was performed using SPIP software. Percentages corresponding to highest occurrences for each time point are indicated in bold.

TABLE 1

| Heights | 0 hr | 1 day | 2 d | 3 d | 5 d | 8 d |
|---|---|---|---|---|---|---|
| A. Aβ40 Alone | | | | | | |
| <1 nm | 98.7 | 0.8 | 0 | 0.1 | 0 | 0 |
| 1-2 nm | 1.3 | 76.2 | 2.8 | 4.5 | 0.9 | 0.1 |
| 2-3 nm | 0 | 21.8 | 92.5 | 82.4 | 17.2 | 0.3 |
| 3-4 nm | 0 | 0.9 | 3.4 | 11.7 | 69.5 | 4.8 |
| >4 nm | 0 | 0.3 | 1.3 | 1.3 | 12.4 | 94.8 |
| B. Aβ40 co-incubated with C6 | | | | | | |
| 0-1 nm | | 43.6 | 10.8 | 0.1 | 0.4 | 0.1 |
| 1-2 nm | | 26.2 | 36.3 | 6.0 | 19.6 | 39.2 |
| 2-3 nm | | 14.2 | 25.5 | 56.8 | 77.4 | 59.6 |
| 3-4 nm | | 6.5 | 22.1 | 34.3 | 2.0 | 0.8 |
| >4 nm | | 9.5 | 5.3 | 2.8 | 0.6 | 0.2 |

Since the in vitro Aβ aggregates are not SDS-stable, when the Aβ samples corresponding to different time points of aggregation are separated on a 10% Tris/Tricine gel containing SDS, all lanes showed a strong band corresponding to monomeric A/3 (FIG. 9A). However, when the Aβ samples were incubated with C6 nanobody a distinct reduction in monomeric Aβ levels was observed with time (FIG. 9A). Low intensity bands corresponding to Aβ aggregates of sizes 28 kD, 40 kD and 56 kD could be observed (FIG. 9B) indicating that co-incubation with C6 generates SDS-stable oligomers similar to the oligomers generated in vivo.

Effect of C6 Nanobodies on Aβ Induced Cytotoxicity Towards SH-SY5Y Neuroblastoma Cells.

Figure 10:
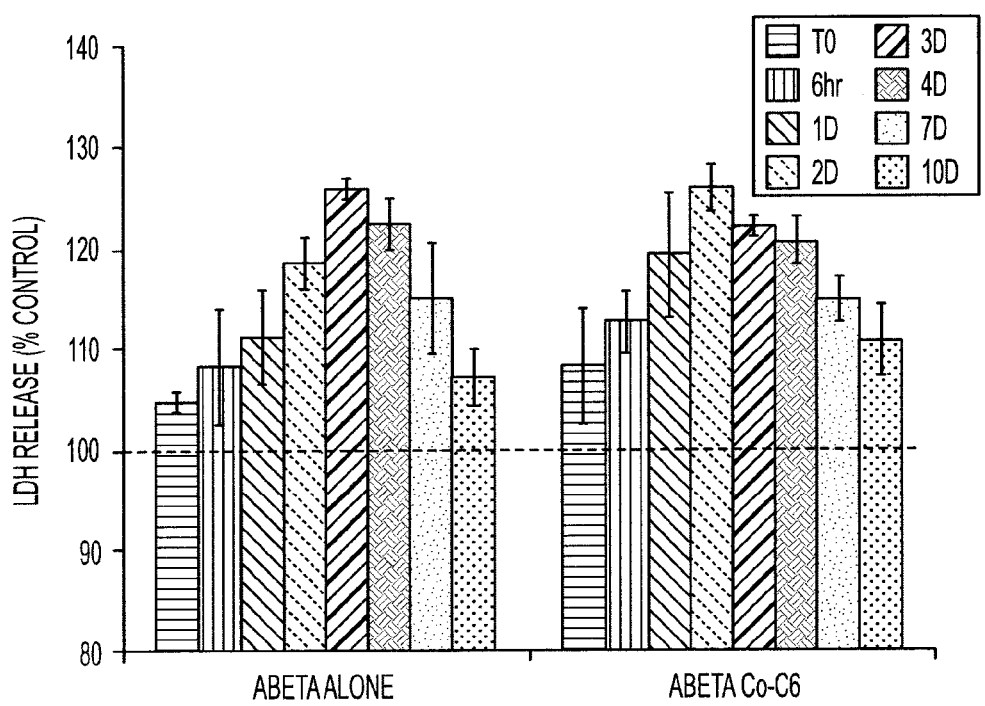
FIG. 10. C6 stabilizes toxic oligomeric form of Aβ. Co-incubation of 50 μM Aβ with 5 μM C6 maintains Aβ-induced toxicity towards SH-SY5Y human neuroblastoma cells. The final concentrations of Aβ and C6 nanobody added to the cells were 1 μM and 0.1 μM respectively. The error bars indicate SEM. Line at 100% indicates cells incubated with buffer alone.

Since C6 nanobody blocks aggregation of Aβ into fibrils, but stabilizes the formation of an oligomeric species, we determined whether C6 nanobody alters cytotoxicity of Aβ aggregates toward a SH-SY5Y neuroblastoma cell line. Cells treated with Aβ alone showed an expected increase in toxicity when incubated with oligomeric Aβ, with peak toxicity observed at 3 and 4 days of aggregation when 2-3 nm oligomeric Aβ concentration are highest (FIG. 10). As the particle height increased upon further aggregation into proto-fibrils and fibrils after 7 and 10 days, a reduction in toxicity was observed. Incubation of cells with the Aβ samples co-incubated with C6 nanobody showed similar toxic effects, with toxicity slightly increasing at earlier time points suggesting that the 2-3 nm aggregate species stabilized by incubating Aβ with C6 nanobody are toxic to the neuronal cell line (FIG. 10).

C6 Nanobody Recognizes Aβ Aggregates in Brain Tissue.

To determine whether C6 nanobody could also recognize small oligomeric Aβ aggregates in brain tissue, we tested different age mouse brain tissue from wild type and triple transgenic (3× Tg) mice developed by LaFerla et al. (34). Brain extracts from Aβ over-expressing transgenic mice (Tg2576) and control mice were homogenized and run on a 10% Tris-Tricine gel, and transferred onto a nitro-cellulose membrane for western blot analysis. The membrane was probed with C6 nanobody using a 9E10-biotin primary and streptavidin-HRP as secondary antibody and stained with DAB (Sigma). Staining intensity of bands corresponding to 40 kDa was quantified using ImageJ software and compared to the background. Samples with standard deviation a) <2 times background are denoted as –; b) 2-3 times background as +; and c) 3-4 times background as ++ and d) >4 times background as +++. Thus, when the tissues were probed with C6 nanobody, strong reactivity was observed with 22 and 27 weeks old 3× Tg samples, while little or no binding was observed with similar aged mice or 68.4 week 3× Tg mice (Table 2).

TABLE 2

C6 reactivity with mouse brain samples

| Mouse Type | Age | Reactivity |
| --- | --- | --- |
| Wild Type | 22 wks | – |
| Wild Type | 28.7 wks | – |
| Transgenic | 10 wks | ++ |
| Transgenic | 22 wks | +++ |
| Transgenic | 27.3 wks | +++ |
| Transgenic | 68.4 wks | + |

Next, the C6 antibody fragment was reacted with blotted aliquots of soluble homogenized samples obtained from healthy (ND) or AD human brain tissue. Brain extracts from the medial temporal gyrus of Non Diseased patients (ND) and Alzheimer's Disease patients (AD) were homogenized and deposited onto a nitrocellulose membrane and probed with C6 nanobody. Staining intensity of the dot blot was quantified using ImageJ software and compared to the background. Samples with standard deviation a) <2 times background are denoted as –; b) 2-3 times background as +; and c) 3-4 times background as ++ and d) >4 times background as +++. Thus, C6 reacted strongly with brain tissue from AD patients who had moderate plaque frequency, but showed little or no reaction with brain tissue from AD patients with severe plaques or with the ND patients (Table 3).

TABLE 3

C6 reactivity with human brain samples

| Sample | Sample Description | Reactivity |
| --- | --- | --- |
| ND1 | No plaque | – |
| ND2 | No plaque | – |
| ND3 | No plaque | + |
| ND4 | Moderate Frequency Plaque | – |
| ND5 | Moderate Frequency Plaque | – |
| ND6 | Moderate Frequency Plaque | + |
| AD1 | Moderate Frequency Plaque | ++ |
| AD2 | Moderate Frequency Plaque | +++ |
| AD3 | Moderate Frequency Plaque | ++ |
| AD4 | Severe Plaques | + |
| AD5 | Severe Plaques | – |
| AD6 | Severe Plaques | – |

Discussion

According to the amyloid cascade hypothesis, neuronal death in AD is a consequence of accumulation and deposition of Aβ which could result either from its over-production or reduced clearance (35). Fibrillar forms of Aβ are the major pathological features of AD, and were initially thought to be responsible for neurodegeneration (36-37). However, numerous studies implicate small soluble Aβ aggregates as the relevant toxic species. For example passive immunization of transgenic mouse models with antibodies against Aβ showed recovery of memory loss without reduction of amyloid plaque burden (23-24). SDS-stable Aβ dimers and trimers were extracted in the soluble fraction from human AD brain and extracts of amyloid plaques (38-41). These low-n SDS-stable Aβ oligomers were implicated in the inhibition of hippocampal LTP in rats (18), impairment of short term memory (19), affected the dendritic morphology in neuronal cells by causing synaptic losses (20) and correlated strongly with dementia in AD patients (14). These studies suggest that these low-n SDS-stable Aβ oligomers are involved in AD, and reagents that recognize this Aβ aggregate species can be valuable therapeutic and diagnostic tools.

Single chain variable domain (scFv) antibodies represent a therapeutic approach that can avoid the inflammatory responses seen with conventional antibodies and can be selected to have specificity for target morphologies. The inventors previously developed a novel bio-panning technique combining atomic force microscopy and phage display technology (25) that enabled isolation of antibody fragments against specific morphologies of Aβ (28). The bio-panning was performed against synthetic Aβ oligomers generated in vitro. In order to isolate antibody fragments against the synapto-toxic naturally derived low-n SDS-stable Aβ oligomers, the panning protocol (FIG. 1) was modified since the brain derived oligomeric Aβ aggregates were available only in very limited amounts (nanograms) and were enriched but not purified.

We included several negative panning steps to eliminate phage binding to off-target antigens. Negative panning was performed against brain derived proteins and monomeric Aβ, and also against synthetic Aβ. The negative panning steps enabled us to eliminate virtually all phage bound to off-target antigens, and allowed for isolation of phage that bind specifically to the brain derived oligomers using minimal target sample (FIG. 2). After a single round of positive panning, we isolated approximately 400 clones from a starting phage library of $10^{12}$ clones. Phage from each of the 400 clones was independently amplified to enable phage from all the clones to amplify to the same extent, then pooled and assayed to verify specificity for the target antigen, and was observed to bind specifically to the target antigen (FIG. 3).

Since availability of antigen was limited, we modified the screening protocol to facilitate isolation of high affinity clones. At low antigen concentrations, phage will compete for antigen sites and high affinity phage will preferentially bind over low affinity clones. The high affinity screen resulted in identification of 18 unique sequences. Further selection of these 18 clones was based on protein expression levels; identifying the C6 clone for further studies (FIG. 4).

Specificity of the C6 phage for the brain derived Aβ oligomers (but not off-target antigens or synthetic Aβ oligomers) was verified by AFM (FIG. 5). We previously identified a nanobody, A4, that specifically recognized oligomeric Aβ species generated in vitro (28). Here we show that the brain derived SDS-stable Aβ oligomers recognized by the C6 nanobody represents a different, conformationally distinct small soluble Aβ aggregate species. All these aggregate species are present selectively in human AD brain tissue (13, 28) indicating that these are a variety of different Aβ aggregate species generated in human tissue and that there may be multiple toxic species and mechanisms.

When incubated with monomeric Aβ, the C6 nanobody inhibits fibril formation (FIG. 7, 8) but shifts the equilibrium from larger to smaller oligomers, stabilizing formation of a 2-3 nm Aβ oligomeric aggregate (Table 1) which was significantly toxic to neuroblastoma cells (FIG. 10). The Aβ oligomers generated in the presence of C6 nanobodies are SDS-stable (FIG. 9), similar to the brain derived Aβ oligomers, suggesting that the small low-n SDS-stable oligomers in the brain are potentially being generated by interacting with certain brain proteins similar to the C6 nanobody. This ability of C6 nanobodies to generate SDS-stable oligomers is uniquely different from other oligomer Aβ specific antibodies which have been previously described by our group.

Western blot analysis revealed that the C6 nanobody recognized a 12-16 kDa Aβ oligomeric species produced by the 7PA2 cell line that over-expressed hAPP (FIG. 6) indicating that C6 nanobody recognized a trimeric or tetrameric form of naturally derived SDS-stable Aβ. Further, height distribution analysis revealed that the size of the oligomeric species recognized by the C6 nanobody in FIG. 5A was 2.1 nm, corresponding to the height of a photo-cross-linked tetrameric form of Aβ (42). These results, together with the western blot in FIG. 9 indicated that the small, SDS-stable, low-n oligomeric morphology of Aβ recognized by the C6 nanobody was a tetramer.

C6 nanobodies could also recognize Aβ in the brain tissue of 3× Tg mouse models of AD, as well from AD brain patients. When used to probe brain extracts from ND and AD patients, C6 nanobodies strongly reacted with extracts from AD patients diagnosed with moderate frequency plaques, but not with extracts from AD patients with severe plaques or with extracts from ND patients. These results indicate that morphology-specific and protein-specific reagent C6 nanobody can differentiate which protein aggregate species are involved in different stages of disease. Reagents such as the C6 nanobody can be very useful tools to more accurately diagnose neurodegenerative diseases and may help to monitor progression and treatment of AD.

Here we demonstrated that a novel bio-panning protocol could effectively be used to isolate nanobodies against specific protein morphologies even when the target antigen was only available in trace amounts and could not be purified. The results indicate there are multiple different morphologically distinct oligomeric Aβ species that naturally occur in human tissue and that they can have distinctly different cytotoxicity effects. Such highly selective morphology specific reagents represent powerful tools that have important diagnostic and therapeutic applications for neurodegenerative diseases.

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

REFERENCES

1. Hardy, J., and Selkoe, D. J. (2002) The amyloid hypothesis of Alzheimer's disease: progress and problems on the road to therapeutics, Science 297, 353-356.
2. Kang, J., Lemaire, H. G., Unterbeck, A., Salbaum, J. M., Masters, C. L., Grzeschik, K. H., Multhaup, G., Beyreuther, K., and Muller-Hill, B. (1987) The precursor of Alzheimer's disease amyloid A4 protein resembles a cell-surface receptor, Nature 325, 733-736.
3. Golde, T. E., Estus, S., Younkin, L. H., Selkoe, D. J., and S. G., Y. (1992) Processing of the Amyloid Protein Precursor to Potentially Amyloidogenic Derivatives, Science 255, 728-730.
4. Estus, S., Golde, T. E., Kunishita, T., Blades, D., Lowery, D., Eisen, M., Usiak, M., Qu, X., Tabira, T., Greenberg, B. D., and Younkin, S. G. (1992) Potentially Amyloidogenic, Carboxyl-Terminal Derivatives of the Amyloid Protein Precursor, Science 255, 726-728.
5. Yankner, B. A. (1996) Mechanisms of Neuronal Degeneration in Alzheimer's Disease., Neuron 16, 921-923.

6. Harper, J. D., and Lansbury, P. T. J. (1997) Models of amyloid seeding in Alzheimer's disease and Scrapie: mechanistic truths and physiological consequences of the time-dependent solubility of amyloid proteins, Annu. Rev. Biochem. 66, 385-407.
7. Harper, J. D., Wong, S. S., Lieber, C. M., and Lansbury, P. T. J. (1997) Observation of metastable Aβ amyloid protofibrils by atomic force microscopy, Chemistry & Biology 4, 119-125.
8. Lambert, M. P., Barlow, A. K., Chromy, B. A., Edwards, C., Freed, R., Liosatos, M., Morgan, T. E., Rozovsky, I., Trommer, B., Viola, K. L., Wals, P., Zhang, C., Finch, C. E., Krafft, G. A., and Klein, W. L. (1998) Diffusible, nonfibrillar ligands derived from Abeta1-42 are potent central nervous system neurotoxins, Proc Natl Acad Sci USA 95, 6448-6453.
9. Caughey, B., and Lansbury, P. T. (2003) Protofibrils, pores, fibrils, and neurodegeneration: separating the responsible protein aggregates from the innocent bystanders, Annu Rev Neurosci 26, 267-298.
10. Lambert, M. P., Barlow, A. K., Chromy, B. A., Edwards, C., Freed, R., Liosatos, M., Morgan, T. E., Rozovsky, I., Trommer, B., Viola, K. L., Wals, P., Zhang, C., Finch, C. E., Krafft, G. A., and Klein, W. L. (1998) Diffusible, nonfibrillar ligands derived from Abeta1-42 are potent central nervous system neurotoxins, Proc Natl Acad Sci USA 95, 6448-6453.
11. Gong, Y., Chang, L., Viola, K. L., Lacor, P. N., Lambert, M. P., Finch, C. E., Krafft, G. A., and Klein, W. L. (2003) Alzheimer's disease-affected brain: presence of oligomeric A beta ligands (ADDLs) suggests a molecular basis for reversible memory loss, Proc Natl Acad Sci USA 100, 10417-10422.
12. Zameer, A., Schulz, P., Wang, M. S., and Sierks, M. R. (2006) Single chain Fv antibodies against the 25-35 Abeta fragment inhibit aggregation and toxicity of Abeta42, Biochemistry 45, 11532-11539.
13. Shankar, G. M., Li, S., Mehta, T. H., Garcia-Munoz, A., Shepardson, N. E., Smith, I., Brett, F. M., Farrell, M. A., Rowan, M. J., Lemere, C. A., Regan, C. M., Walsh, D. M., Sabatini, B. L., and Selkoe, D. J. (2008) Amyloid-beta protein dimers isolated directly from Alzheimer's brains impair synaptic plasticity and memory, Nat Med 14, 837-842.
14. Mc Donald, J. M., Savva, G. M., Brayne, C., Welzel, A. T., Forster, G., Shankar, G. M., Selkoe, D. J., Ince, P. G., and Walsh, D. M. (2010) The presence of sodium dodecyl sulphate-stable Abeta dimers is strongly associated with Alzheimer-type dementia, Brain 133, 1328-1341.
15. Walsh, D. M., Tseng, B. P., Rydel, R. E., Podlisny, M. B., and Selkoe, D. J. (2000) The oligomerization of amyloid beta-protein begins intracellularly in cells derived from human brain, Biochemistry 39, 10831-10839.
16. Lesne, S., Koh, M. T., Kotilinek, L., Kayed, R., Glabe, C. G., Yang, A., Gallagher, M., and Ashe, K. H. (2006) A specific amyloid-beta protein assembly in the brain impairs memory, Nature 440, 352-357.
17. Kawarabayashi, T., Shoji, M., Younkin, L. H., Wen-Lang, L., Dickson, D. W., Murakami, T., Matsubara, E., Abe, K., Ashe, K. H., and Younkin, S. G. (2004) Dimeric amyloid beta protein rapidly accumulates in lipid rafts followed by apolipoprotein E and phosphorylated tau accumulation in the Tg2576 mouse model of Alzheimer's disease, J Neurosci 24, 3801-3809.
18. Walsh, D. M., Klyubin, I., Fadeeva, J. V., Cullen, W. K., Anwyl, R., Wolfe, M. S., Rowan, M. J., and Selkoe, D. J. (2002) Naturally secreted oligomers of amyloid beta protein potently inhibit hippocampal long-term potentiation in vivo, Nature 416, 535-539.
19. Cleary, J. P., Walsh, D. M., Hofmeister, J. J., Shankar, G. M., Kuskowski, M. A., Selkoe, D. J., and Ashe, K. H. (2005) Natural oligomers of the amyloid-beta protein specifically disrupt cognitive function, Nat Neurosci 8, 79-84.
20. Shankar, G. M., Bloodgood, B. L., Townsend, M., Walsh, D. M., Selkoe, D. J., and Sabatini, B. L. (2007) Natural oligomers of the Alzheimer amyloid-beta protein induce reversible synapse loss by modulating an NMDA-type glutamate receptor-dependent signaling pathway, J Neurosci 27, 2866-2875.
21. O'Hare, E., Weldon, D. T., Mantyh, P. W., Ghilardi, J. R., Finke, M. P., Kuskowski, M. A., Maggio, J. E., Shephard, R. A., and Cleary, J. (1999) Delayed behavioral effects following intrahippocampal injection of aggregated A beta (1-42), Brain Res 815, 1-10.
22. Cleary, J., Hittner, J. M., Semotuk, M., Mantyh, P., and O'Hare, E. (1995) Beta-amyloid (1-40) effects on behavior and memory, Brain Res 682, 69-74.
23. Dodart, J. C., Bales, K. R., Gannon, K. S., Greene, S. J., DeMattos, R. B., Mathis, C., DeLong, C. A., Wu, S., Wu, X., Holtzman, D. M., and Paul, S. M. (2002) Immunization reverses memory deficits without reducing brain Abeta burden in Alzheimer's disease model, Nat Neurosci 5, 452-457.
24. Kotilinek, L. A., Bacskai, B., Westerman, M., Kawarabayashi, T., Younkin, L., Hyman, B. T., Younkin, S., and Ashe, K. H. (2002) Reversible memory loss in a mouse transgenic model of Alzheimer's disease, J Neurosci 22, 6331-6335.
25. Barkhordarian, H., Emadi, S., Schulz, P., and Sierks, M. R. (2006) Isolating recombinant antibodies against specific protein morphologies using atomic force microscopy and phage display technologies, Protein Eng Des Sel 19, 497-502.
26. Emadi, S., Barkhordarian, H., Wang, M. S., Schulz, P., and Sierks, M. R. (2007) Isolation of a human single chain antibody fragment against oligomeric alpha-synuclein that inhibits aggregation and prevents alpha-synuclein-induced toxicity, J Mol Biol 368, 1132-1144.
27. Emadi, S., Kasturirangan, S., Wang, M. S., Schulz, P., and Sierks, M. R. (2009) Detecting morphologically distinct oligomeric forms of alpha-synuclein, J Biol Chem 284, 11048-11058.
28. Zameer, A., Kasturirangan, S., Emadi, S., Nimmagadda, S. V., and Sierks, M. R. (2008) Anti-oligomeric Abeta single-chain variable domain antibody blocks Abeta-induced toxicity against human neuroblastoma cells, J Mol Biol 384, 917-928.
29. Sheets, M. D., Amersdorfer, P., Finnern, R., Sargent, P., Lindquist, E., Schier, R., Hemingsen, G., Wong, C., Gerhart, J. C., and Marks, J. D. (1998) Efficient construction of a large nonimmune phage antibody library: the production of high-affinity human single-chain antibodies to protein antigens, Proc Natl Acad Sci USA 95, 6157-6162.
30. Marks, J. D., Hoogenboom, H. R., Bonnert, T. P., McCafferty, J., Griffiths, A. D., and Winter, G. (1991) By-passing immunization. Human antibodies from V-gene libraries displayed on phage, J Mol Biol 222, 581-597.
31. Wang, M. S., Zameer, A., Emadi, S., and Sierks, M. R. (2009) Characterizing antibody specificity to different protein morphologies by AFM, Langmuir 25, 912-918.

32. Liu, R., Yuan, B., Emadi, S., Zameer, A., Schulz, P., McAllister, C., Lyubchenko, Y., Goud, G., and Sierks, M. R. (2004) Single chain variable fragments against beta-amyloid (Abeta) can inhibit Abeta aggregation and prevent abeta-induced neurotoxicity, Biochemistry 43, 6959-6967.
33. Legrand, C., Bour, J. M., Jacob, C., Capiaumont, J., Martial, A., Marc, A., Wudtke, M., Kretzmer, G., Demangel, C., Duval, D., and et al. (1992) Lactate dehydrogenase (LDH) activity of the cultured eukaryotic cells as marker of the number of dead cells in the medium [corrected], J Biotechnol 25, 231-243.
34. Oddo, S., Caccamo, A., Shepherd, J. D., Murphy, M. P., Golde, T. E., Kayed, R., Metherate, R., Mattson, M. P., Akbari, Y., and LaFerla, F. M. (2003) Triple-transgenic model of Alzheimer's disease with plaques and tangles: intracellular Abeta and synaptic dysfunction, Neuron 39, 409-421.
35. Hardy, J. A., and Higgins, G. A. (1992) Alzheimer's disease: the amyloid cascade hypothesis, Science 256, 184-185.
36. Lorenzo, A., and Yankner, B. A. (1994) Beta-amyloid neurotoxicity requires fibril formation and is inhibited by congo red, Proc Natl Acad Sci USA 91, 12243-12247.
37. Pike, C. J., Burdick, D., Walencewicz, A. J., Glabe, C. G., and Cotman, C. W. (1993) Neurodegeneration induced by beta-amyloid peptides in vitro: the role of peptide assembly state, J Neurosci 13, 1676-1687.
38. McLean, C. A., Chemy, R. A., Fraser, F. W., Fuller, S. J., Smith, M. J., Beyreuther, K., Bush, A. I., and Masters, C. L. (1999) Soluble pool of Abeta amyloid as a determinant of severity of neurodegeneration in Alzheimer's disease, Ann Neurol 46, 860-866.
39. Enya, M., Morishima-Kawashima, M., Yoshimura, M., Shinkai, Y., Kusui, K., Khan, K., Games, D., Schenk, D., Sugihara, S., Yamaguchi, H., and Ihara, Y. (1999) Appearance of sodium dodecyl sulfate-stable amyloid beta-protein (Abeta) dimer in the cortex during aging, Am J Pathol 154, 271-279.
40. Funato, H., Enya, M., Yoshimura, M., Morishima-Kawashima, M., and Ihara, Y. (1999) Presence of sodium dodecyl sulfate-stable amyloid beta-protein dimers in the hippocampus CA1 not exhibiting neurofibrillary tangle formation, Am J Pathol 155, 23-28.
41. Roher, A. E., Chaney, M. O., Kuo, Y. M., Webster, S. D., Stine, W. B., Haverkamp, L. J., Woods, A. S., Cotter, R. J., Tuohy, J. M., Krafft, G. A., Bonnell, B. S., and Emmerling, M. R. (1996) Morphology and toxicity of Abeta-(1-42) dimer derived from neuritic and vascular amyloid deposits of Alzheimer's disease, J Biol Chem 271, 20631-20635.
42. Ono, K., Condron, M. M., and Teplow, D. B. (2009) Structure-neurotoxicity relationships of amyloid beta-protein oligomers, Proc Natl Acad Sci USA 106, 14745-14750.

---

The invention claimed is:

1. An antibody or antibody fragment that specifically binds the 12-16 kDa species of Aβ and wherein the antibody or antibody fragment comprises SEQ ID NO: 1 or amino acid residues 16-292 of SEQ ID NO: 1.

2. A method of inhibiting the aggregation of Aβ comprising contacting a composition that comprises Aβ monomers with the antibody or antibody fragment of claim 1.

3. The method of claim 2, wherein said aggregation of Aβ is in a cell.

4. The method of claim 2, wherein said aggregation of Aβ is in brain tissue.

5. The method of claim 2, wherein said contacting with the antibody or antibody fragment decreases the rate of formation of Aβ aggregates as compared to said rate in the absence the antibody or antibody fragment.

6. A method of detecting the presence of Aβ in a physiological sample comprising contacting a sample with the antibody or antibody fragment of claim 1.

7. The method of claim 6, wherein the physiological sample is brain tissue, serum, cerebrospinal fluid (CSF), urine or saliva.

8. A method of preventing or inhibiting the accumulation of Aβ in the brain of a mammal comprising administering to said mammal the antibody or antibody fragment of claim 1.

* * * * *

SEQUENCE LISTING

```
<160> NUMBER OF SEQ ID NOS: 4

<210> SEQ ID NO 1
<211> LENGTH: 292
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Any amino acid

<400> SEQUENCE: 1

Glu Xaa Pro Ile Ala Tyr Gly Ser Arg Trp Ile Val Ile Thr Arg Gly
1               5                   10                  15

Pro Ala Gly His Gly Pro Gly Thr Ala Ala Gly Val Gly Gly Gly Leu
            20                  25                  30

Val Gln Pro Gly Gly Ser Leu Arg Leu Ser Cys Ala Ala Ser Gly Phe
        35                  40                  45

Thr Phe Ser Ser Tyr Ala Met Ser Trp Val Arg Gln Ala Pro Gly Lys
    50                  55                  60

Gly Leu Glu Trp Val Ser Ala Ile Ser Gly Ser Gly Gly Ser Thr Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Lys Ser Tyr Gly Ser Val Lys Ile Ser Cys
        115                 120                 125

Phe Asp Tyr Trp Gly Gln Ser Thr Leu Val Thr Val Ser Ser Gly Gly
    130                 135                 140
```

```
Gly Gly Ser Gly Gly Gly Ser Gly Gly Gly Ser Glu Ile Val
145                 150                 155                 160

Leu Thr Gln Ser Pro Asp Ser Leu Ala Val Ser Leu Gly Glu Arg Ala
            165                 170                 175

Thr Ile Asn Cys Lys Ser Ser Gln Ser Val Leu Tyr Asn Ser Asn Asn
        180                 185                 190

Lys Asn Tyr Leu Ala Trp Tyr Gln Gln Lys Pro Gly Gln Ser Pro Glu
        195                 200                 205

Leu Leu Ile Tyr Trp Ala Ser Thr Arg Glu Ser Gly Val Pro Asp Arg
    210                 215                 220

Phe Ser Gly Ser Gly Ser Gly Thr Glu Phe Thr Leu Thr Ile Ser Ser
225                 230                 235                 240

Leu Gln Ala Glu Asp Val Ala Val Tyr Tyr Cys Gln Gln Phe Tyr Ser
            245                 250                 255

Thr Pro Pro Thr Phe Gly Gln Gly Thr Lys Leu Glu Ile Lys Arg Ala
            260                 265                 270

Ala Ala His His His His His His Gly Ala Ala Glu Gln Lys Leu Ile
        275                 280                 285

Ser Glu Glu Asp
    290

<210> SEQ ID NO 2
<211> LENGTH: 200
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(200)
<223> OTHER INFORMATION: This sequence may encompass 5-200 residues

<400> SEQUENCE: 2

Gly Gly Gly Gly Gly Gly Gly Gly Gly Gly Gly Gly Gly Gly Gly Gly
1               5                   10                  15

Gly Gly Gly Gly Gly Gly Gly Gly Gly Gly Gly Gly Gly Gly Gly Gly
            20                  25                  30

Gly Gly Gly Gly Gly Gly Gly Gly Gly Gly Gly Gly Gly Gly Gly Gly
        35                  40                  45

Gly Gly Gly Gly Gly Gly Gly Gly Gly Gly Gly Gly Gly Gly Gly Gly
    50                  55                  60

Gly Gly Gly Gly Gly Gly Gly Gly Gly Gly Gly Gly Gly Gly Gly Gly
65                  70                  75                  80

Gly Gly Gly Gly Gly Gly Gly Gly Gly Gly Gly Gly Gly Gly Gly Gly
            85                  90                  95

Gly Gly Gly Gly Gly Gly Gly Gly Gly Gly Gly Gly Gly Gly Gly Gly
        100                 105                 110

Gly Gly Gly Gly Gly Gly Gly Gly Gly Gly Gly Gly Gly Gly Gly Gly
    115                 120                 125

Gly Gly Gly Gly Gly Gly Gly Gly Gly Gly Gly Gly Gly Gly Gly Gly
130                 135                 140

Gly Gly Gly Gly Gly Gly Gly Gly Gly Gly Gly Gly Gly Gly Gly Gly
145                 150                 155                 160

Gly Gly Gly Gly Gly Gly Gly Gly Gly Gly Gly Gly Gly Gly Gly Gly
            165                 170                 175
```

Gly Gly Gly Gly Gly Gly Gly Gly Gly Gly Gly Gly Gly
            180                 185                 190

Gly Gly Gly Gly Gly Gly Gly Gly
        195                 200

<210> SEQ ID NO 3
<211> LENGTH: 201
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(100)
<223> OTHER INFORMATION: This region may encompass 3-100 residues
<220> FEATURE:
<221> NAME/KEY: misc_feature
<222> LOCATION: (102)..(201)
<223> OTHER INFORMATION: This region may encompass 3-100 residues

<400> SEQUENCE: 3

Gly Gly Gly Gly Gly Gly Gly Gly Gly Gly Gly Gly Gly Gly Gly
1               5                   10                  15

Gly Gly Gly Gly Gly Gly Gly Gly Gly Gly Gly Gly Gly Gly Gly
            20                  25                  30

Gly Gly Gly Gly Gly Gly Gly Gly Gly Gly Gly Gly Gly Gly Gly
        35                  40                  45

Gly Gly Gly Gly Gly Gly Gly Gly Gly Gly Gly Gly Gly Gly Gly
    50                  55                  60

Gly Gly Gly Gly Gly Gly Gly Gly Gly Gly Gly Gly Gly Gly Gly
65                  70                  75                  80

Gly Gly Gly Gly Gly Gly Gly Gly Gly Gly Gly Gly Gly Gly Gly
                85                  90                  95

Gly Gly Gly Gly Pro Gly Gly Gly Gly Gly Gly Gly Gly Gly Gly
            100                 105                 110

Gly Gly Gly Gly Gly Gly Gly Gly Gly Gly Gly Gly Gly Gly Gly
        115                 120                 125

Gly Gly Gly Gly Gly Gly Gly Gly Gly Gly Gly Gly Gly Gly Gly
    130                 135                 140

Gly Gly Gly Gly Gly Gly Gly Gly Gly Gly Gly Gly Gly Gly Gly
145                 150                 155                 160

Gly Gly Gly Gly Gly Gly Gly Gly Gly Gly Gly Gly Gly Gly Gly
                165                 170                 175

Gly Gly Gly Gly Gly Gly Gly Gly Gly Gly Gly Gly Gly Gly Gly
            180                 185                 190

Gly Gly Gly Gly Gly Gly Gly Gly Gly
        195                 200

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 4

His His His His His His
1               5